(12) United States Patent
Hoffman et al.

(10) Patent No.: US 12,193,681 B2
(45) Date of Patent: Jan. 14, 2025

(54) MONITORING SYSTEM FOR A HEMOSTASIS BAND

(71) Applicant: Terumo Medical Corporation, Somerset, NJ (US)

(72) Inventors: Brian Hoffman, Princeton, NJ (US); Linda Trask, Newark, DE (US); Katherine Arazawa, Philadelphia, PA (US)

(73) Assignee: Terumo Medical Corporation, Somerset, NJ (US)

( * ) Notice: Subject to any disclaimer, the term of this patent is extended or adjusted under 35 U.S.C. 154(b) by 169 days.

(21) Appl. No.: 17/368,549

(22) Filed: Jul. 6, 2021

(65) Prior Publication Data

US 2023/0012280 A1    Jan. 12, 2023

(51) Int. Cl.
*A61B 17/132* (2006.01)
*A61B 17/135* (2006.01)
*A61B 17/00* (2006.01)
*A61B 17/12* (2006.01)

(52) U.S. Cl.
CPC ........ *A61B 17/1325* (2013.01); *A61B 17/135* (2013.01); *A61B 2017/00022* (2013.01); *A61B 2017/00119* (2013.01); *A61B 2017/00221* (2013.01); *A61B 2017/12004* (2013.01); *A61B 2562/0247* (2013.01)

(58) Field of Classification Search
CPC .............. A61B 17/1325; A61B 17/135; A61B 2017/00022; A61B 2017/00119; A61B 2017/00221; A61B 2017/12004; A61B 2562/0247
See application file for complete search history.

(56) References Cited

U.S. PATENT DOCUMENTS

| | | | |
|---|---|---|---|
| 6,656,136 B1 | 12/2003 | Weng et al. | |
| 9,241,826 B1 | 1/2016 | Shih | |
| 9,924,949 B2 | 3/2018 | Benz et al. | |
| 9,943,316 B2 | 4/2018 | Kornowski et al. | |
| 10,076,462 B2 | 9/2018 | Johnson et al. | |
| 10,758,673 B2 | 9/2020 | Hyde et al. | |
| 2004/0098035 A1* | 5/2004 | Wada .................... | A61B 17/135 606/201 |
| 2004/0147956 A1* | 7/2004 | Hovanes .............. | A61B 5/0225 606/202 |
| 2008/0262533 A1* | 10/2008 | McEwen ............ | A61B 17/1355 606/202 |
| 2008/0306414 A1* | 12/2008 | Petruzzello .......... | A61B 17/135 601/2 |
| 2012/0215075 A1* | 8/2012 | Surace ................. | A61B 5/0002 600/301 |
| 2012/0330112 A1* | 12/2012 | Lamego ............... | A61B 5/0022 600/483 |

(Continued)

FOREIGN PATENT DOCUMENTS

| | | |
|---|---|---|
| CN | 103027671 A | 4/2013 |
| CN | 104287805 A | 1/2015 |

(Continued)

*Primary Examiner* — Anh T Dang

(74) *Attorney, Agent, or Firm* — Quarles & Brady LLP; James J. Aquilina

(57) ABSTRACT

The present application discloses devices and methods for monitoring the performance of a hemostasis device during a hemostatic procedure.

26 Claims, 9 Drawing Sheets

(56) References Cited

U.S. PATENT DOCUMENTS

| | | | |
|---|---|---|---|
| 2014/0012120 A1* | 1/2014 | Cohen | A61B 5/02042 600/371 |
| 2014/0230827 A1 | 8/2014 | Jobe et al. | |
| 2015/0201948 A1* | 7/2015 | Kornowski | A61B 17/1355 606/203 |
| 2015/0221238 A1 | 8/2015 | Huebner | |
| 2016/0038154 A1 | 2/2016 | Cohen et al. | |
| 2017/0150972 A1 | 6/2017 | Kruk | |
| 2018/0014832 A1* | 1/2018 | Lampropoulos | A61B 17/135 |
| 2018/0193031 A1 | 7/2018 | Du et al. | |
| 2018/0214160 A1 | 8/2018 | Hoskins et al. | |

FOREIGN PATENT DOCUMENTS

| | | |
|---|---|---|
| CN | 103654907 B | 1/2016 |
| CN | 103815945 B | 3/2016 |
| CN | 103815940 B | 4/2016 |
| CN | 206228391 U | 6/2017 |
| CN | 107252336 A | 10/2017 |
| CN | 107496002 A | 12/2017 |
| CN | 107822687 A | 3/2018 |
| CN | 208371844 U | 1/2019 |
| CN | 208404728 U | 1/2019 |
| CN | 105943105 B | 2/2019 |
| CN | 109745095 A | 5/2019 |
| CN | 208864401 U | 5/2019 |
| CN | 209847294 U | 12/2019 |
| IN | 104095663 B | 6/2017 |
| IN | 209404865 U | 9/2019 |
| KR | 101787607 B1 | 10/2017 |
| WO | 1998046144 A1 | 10/1998 |
| WO | 2011096336 A1 | 8/2011 |
| WO | 2014036531 A1 | 3/2014 |
| WO | 2017140024 A1 | 8/2017 |

\* cited by examiner

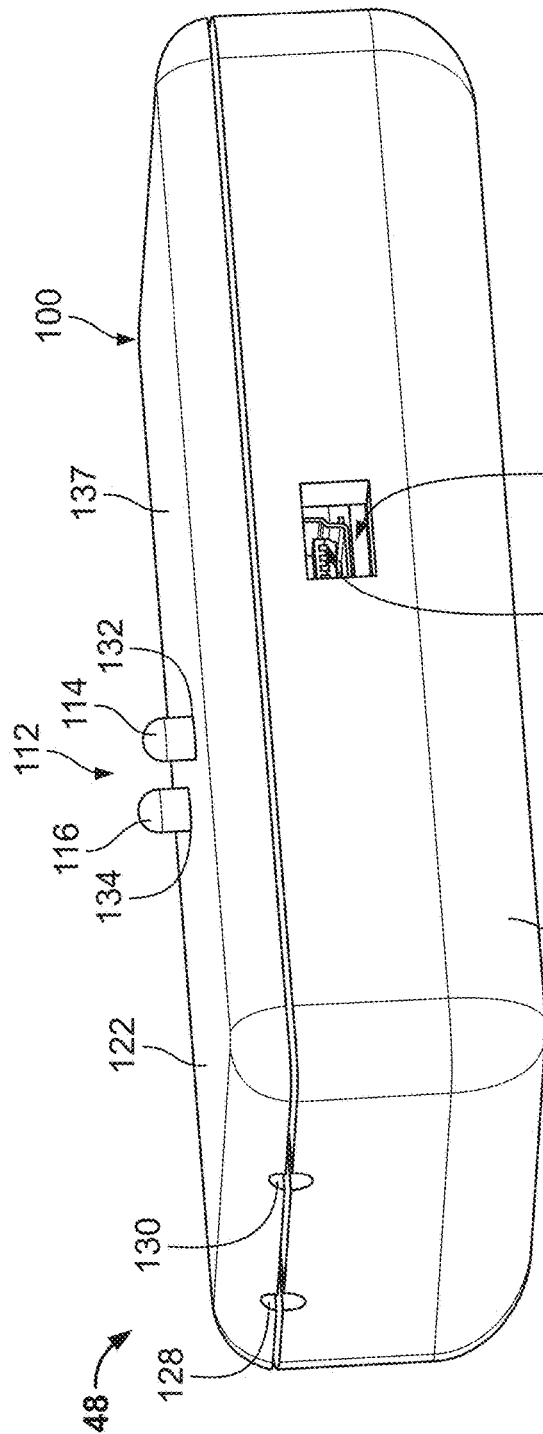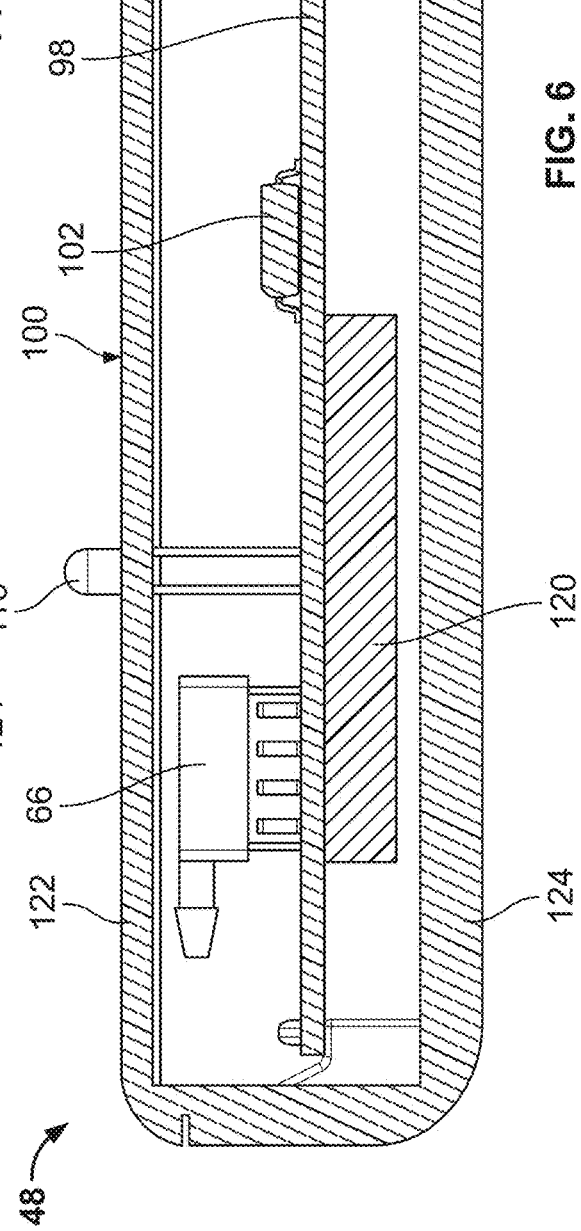

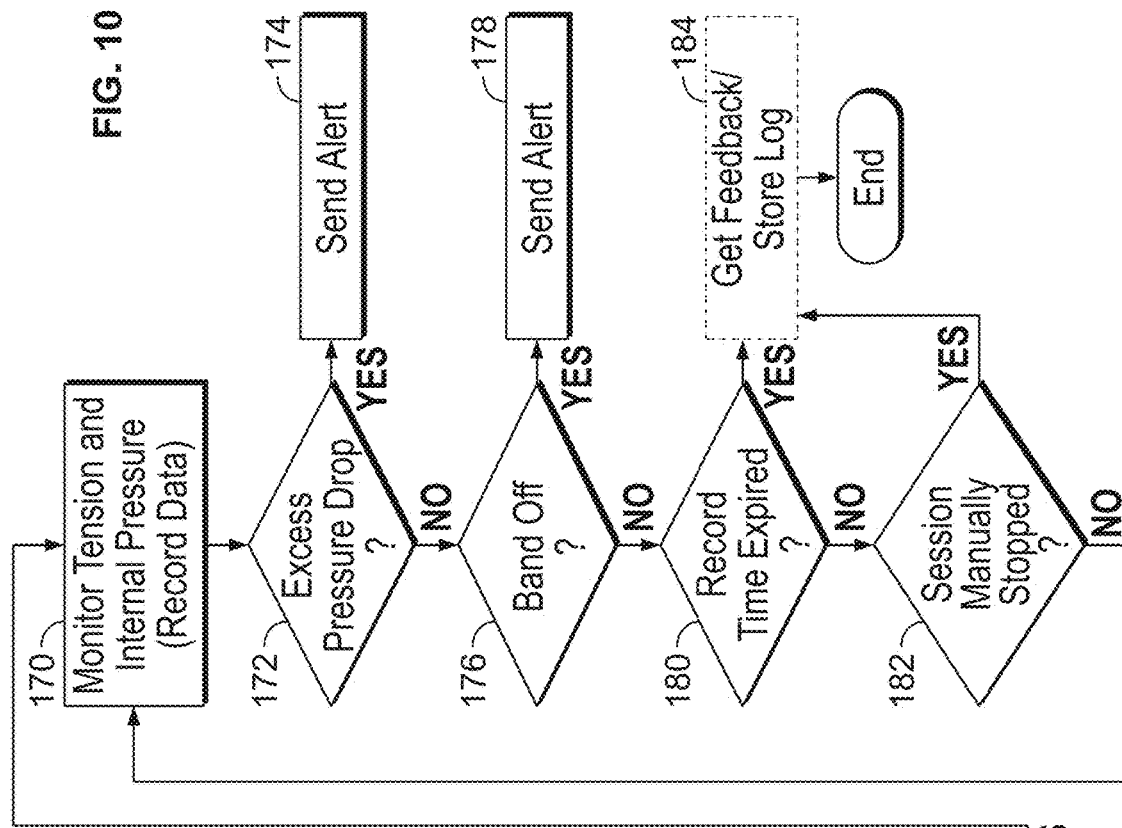
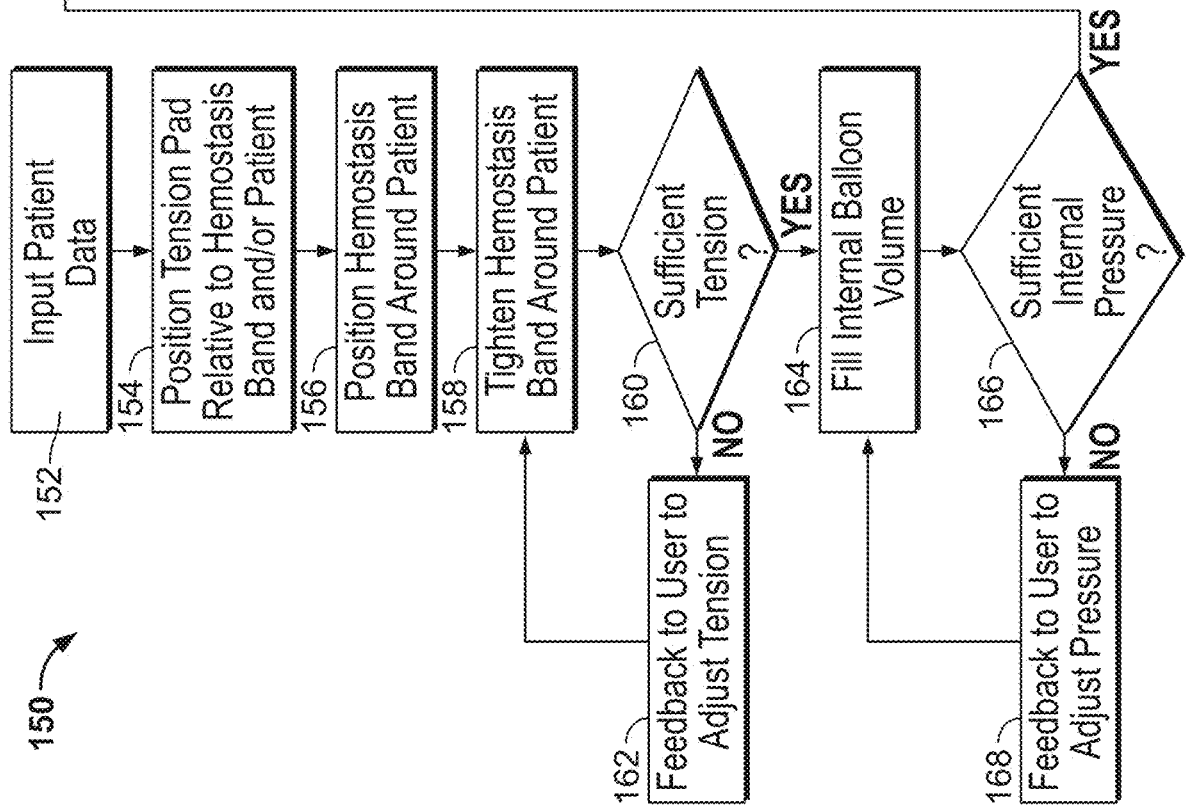
FIG. 10

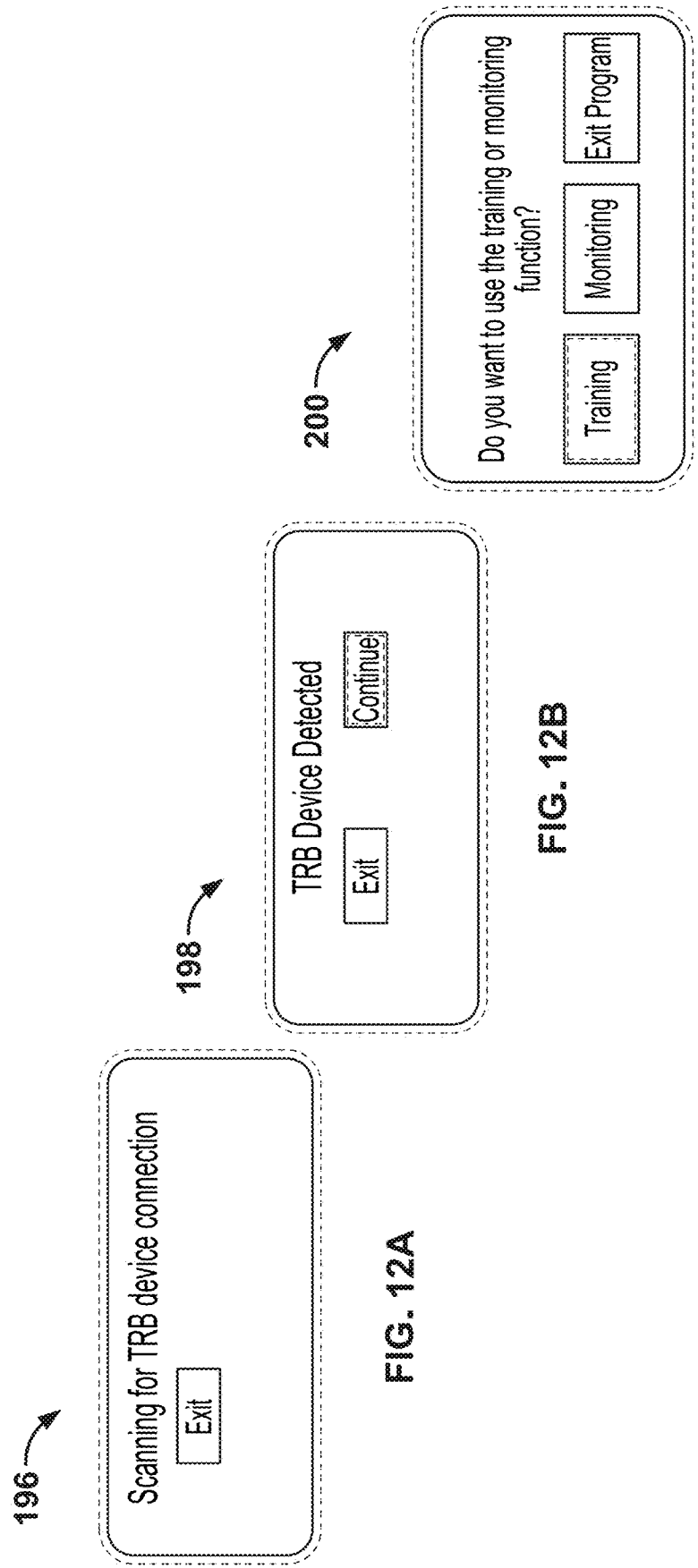

MONITORING SYSTEM FOR A HEMOSTASIS BAND

BACKGROUND

The present invention relates to a hemostasis band that is adapted to act as a compression device to promote hemostasis at an endovascular access site, and more particularly to a monitoring system for a hemostasis band to provide feedback to a clinician regarding band status and performance.

After an endovascular procedure involving arterial or venous access, it may be desirable or necessary to apply pressure to the access site to promote hemostasis, for example, using a hemostasis band. Some existing hemostasis bands are tightened around the access site, then one or more balloons are inflated to compress the band against the access site. Clinicians generally provide the same volume of air to inflate the balloon(s) when the band is applied to a patient, yet the resulting pressure applied to the access site can vary greatly, for example, due to patient physiological variables or variability in the initial hemostasis band tension. This increased variability can lead to delayed hemostasis, re-bleed, hematoma, patient discomfort, or other issues.

Accordingly, there is a need for a monitoring system for a hemostasis band and methods for monitoring band performance that address these and other drawbacks of the prior art.

SUMMARY OF THE DISCLOSURE

In one respect, the present disclosure comprises a hemostatic device comprising: a hemostasis band including a main body adapted to be wrapped and releasably secured around at least one portion of a body part of a patient, and a compression element adapted to apply a targeted pressure to at least one artery or vein located in the body part; and a hemostasis band monitoring system including a pressure monitoring component incorporating a first sensor, the first sensor being adapted to detect a first measurement indicative of the targeted pressure that is being applied to the at least one artery or vein.

In another respect, the present disclosure comprises a hemostatic device comprising: a hemostasis band including a main body adapted to be wrapped and releasably secured around at least one portion of a body part of a patient, and an inflatable balloon assembly adapted to apply targeted pressure to at least one artery or vein located in the at least one portion of the body part; and a hemostasis band monitoring system including a first sensor adapted to sense a first measurement indicative of a tightness of the main body when it is wrapped and releasably secured around the at least one portion of the body part, a second sensor adapted to sense a second measurement indicative of an internal pressure that is present within the inflatable balloon assembly, and a controller in communication with the first sensor and the second sensor to receive the first measurement and the second measurement, respectively, the controller being configured to analyze the first measurement and the second measurement and provide feedback to a user relating the first measurement to an optimal tightness for the main body and relating the second measurement to an optimal internal pressure for the inflatable balloon assembly.

In yet another respect, the present disclosure comprises a method of using a hemostasis band monitoring system with a hemostasis band to perform a hemostatic procedure on at least one artery or vein located in at least one body part of a patient, the method comprising: wrapping and releasably securing a main body of the hemostasis band around the at least one body part of the patient, the hemostasis band further comprising a compression element adapted to apply targeted pressure to the at least one artery or vein and a pressure monitoring component, the pressure monitoring component being in communication with a first sensor, the first sensor being adapted to detect a first measurement indicative of the targeted pressure that is being applied to the at least one artery or vein; and locating a second sensor at least partially between the main body of the hemostasis band and the at least one body part, the second sensor being adapted to detect a second measurement indicative of a tightness of the main body when it is wrapped and releasably secured around the at least one portion of the body part.

In yet another respect, the present disclosure comprises a hemostatic device comprising: a hemostasis band including a main body adapted to be wrapped and releasably secured around at least one portion of a body part of a patient, and a compression element adapted to apply a targeted pressure to at least one artery or vein located in the body part; and a hemostasis band monitoring system incorporating a sensor adapted to detect a measurement indicative of the targeted pressure that is being applied to the at least one artery or vein.

BRIEF DESCRIPTION OF THE DRAWINGS

The present disclosure will hereinafter be described in conjunction with the appended drawing figures, wherein like numerals denote like elements.

FIG. 5 is a perspective view of a monitoring unit of the hemostasis band monitoring system of FIG. 2;

FIG. 6 is a cross-sectional view of the monitoring unit of FIG. 5, taken lengthwise through the center of the housing of the monitoring unit;

FIG. 10 is a flow chart illustrating a method, according to one embodiment of the disclosure, of performing a hemostatic procedure using the hemostasis band monitoring system according to the present disclosure;

FIG. 11A is a screen illustration showing band tightening feedback provided to a user and FIG. 11B is a screen illustration showing balloon pressure feedback provided to a user; and FIGS. 12A-12C are screen illustrations showing a graphical user interface of the hemostasis band monitoring system, where FIG. 12A is a screen illustration showing a scanning operation of a monitoring system program, FIG. 12B is a screen illustration showing a device detection query of the monitoring system program, and FIG. 12C is a screen illustration showing a function query of the monitoring system program.

DETAILED DESCRIPTION OF THE EMBODIMENT(S)

Figure 1:
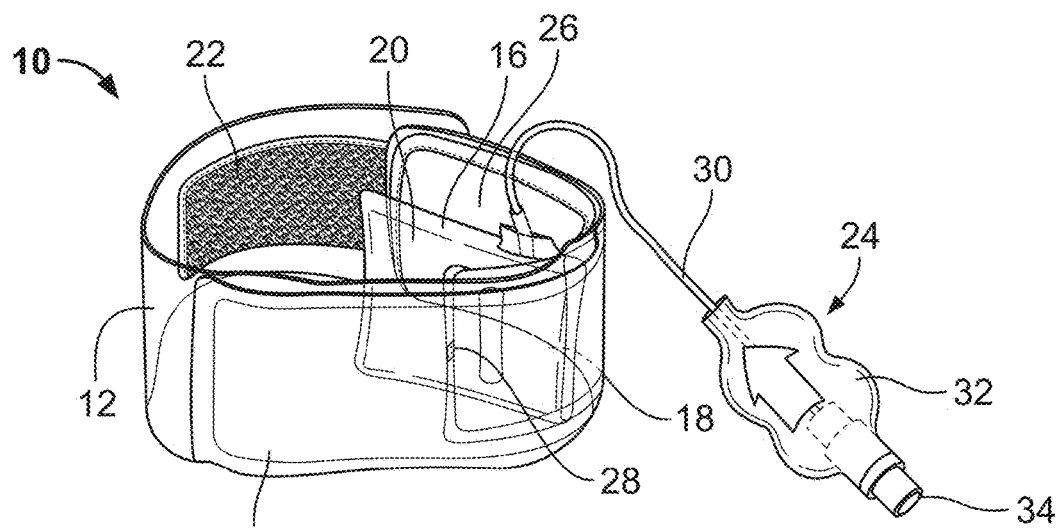
FIG. 1 is a perspective view of a hemostasis band according to the prior art, in an "as-used" configuration.

The ensuing detailed description provides exemplary embodiment(s) only, and is not intended to limit the scope, applicability, or configuration thereof. Rather, the ensuing detailed description of the exemplary embodiment(s) will provide those skilled in the art with an enabling description for implementing these embodiment(s). It should be understood that various changes may be made in the function and arrangement of elements of the embodiment(s) without departing from the spirit and scope of the invention, as set forth in the appended claims.

Directional terms (e.g., upper, lower, left, right, etc.) may be used herein. These directional terms are merely intended to assist in disclosing the embodiment(s) and claiming the invention and are not intended to limit the claimed invention in any way. In addition, reference numerals that are introduced in the specification in association with a drawing figure may be repeated in one or more subsequent figure(s) without additional description in the specification, in order to provide context for other features.

For purposes of the present specification and claims, the term "inflatable" should be understood to mean fillable with a fluid, including but not limited to air. Further, for purposes of the present specification and claims, the term "access site" should be understood to refer to a site where arterial, venous, or other vascular access has occurred on a patient.

Peripheral vascular interventions are commonly used for treating occluded vessels, ballooning, atherectomy, and stenting. For example, antegrade access via the radial artery in a patient's wrist is common, and various retrograde approaches upwardly from below a patient's knee are also established procedures. After such an intervention, the vascular (i.e., either arterial or venous) access site is typically closed through application of pressure to encourage hemostasis, while maintaining patency in the vascular pathway.

Hemostatic devices that are wrapped around a patient's limb at a site on the limb where bleeding is to be stopped, and which include one or more inflatable balloons or bladders that target pressure at a vascular access site, are known in the art. Multiple embodiments of one such hemostatic device and methods of using such devices are described in U.S. Pat. No. 7,498,477, the entirety of which is incorporated by reference as if set forth herein.

For example, FIG. 1 illustrates a hemostasis band 10 in accordance with the prior art. The hemostasis band 10 (i.e., the TR Band sold by Terumo Kabushiki Kaisha of Tokyo, Japan), as well as some other known hemostasis bands, are indicated for use on the radial artery. Accordingly, these products are designed to fit the wrist area, while directing the force of a compression element thereof appropriately to the radial artery, while protecting the ulnar area from uncomfortable pressure. In this prior art device, the hemostasis band 10 includes a main body 12, a rigid plate 14, a compression element 16 (i.e., a balloon assembly) that includes two inflatable balloons 18, 20, a fastener 22, and an inflation port assembly 24.

The main body 12 is designed to be wrapped and adjustably secured in place around a wrist of a patient via the fastener 22. In this example, the fastener 22 includes complementary patches of hook-and-loop type fasteners (e.g., Velcro®) that permit for the size (i.e., circumference) of the hemostasis band 10 to be adjusted for use on patients with a wide range of limb circumferences. While the main body 12 may comprise a substantially flexible material to account for wrapping around the patient's limb, the rigid plate 14 may be constructed of a more rigid material that maintains a substantially fixed shape. The rigid plate 14 may be coupled to the main body 12 and oriented such that compression can be applied to the radial artery and not affect the ulnar artery. It should also be noted that, in some applications, the hemostasis band 10 may not include a rigid plate 14.

As also shown in FIG. 1, the compression element 16 may be coupled to and positioned along an interior surface 26 of the main body 12 (i.e., facing the patient's wrist when the hemostasis band 10 is attached thereto). Furthermore, the compression element 16 may be positioned along the main body 12 substantially opposite the rigid plate 14 such that the compression element 16 is located between the rigid plate 14 and the at least one artery or vein where the vascular access site is located when the hemostasis band 10 is attached.

Generally, the compression element 16 includes a dual-balloon configuration, as described in U.S. Pat. No. 7,498,477, which supports a process to titrate air and reduce compression (pressure) during recovery, allowing for the artery or vein to remain patent over time, while achieving hemostasis. For example, the compression element 16 is comprised of a main balloon 18 and a secondary balloon 20 fluidly connected to one another so that the secondary balloon 20 inflates as the main balloon 18 inflates. The balloons 18, 20 may be inflated so that the secondary balloon 20 provides oblique pressure against the main balloon 18, which in turn provides targeted pressure to the vascular access site, thus promoting hemostasis. The rigid plate 14 acts to direct the pressure created by the inflated balloons 18, 20 towards the vascular access site, instead of permitting this pressure to displace or stretch the main body 12 of the hemostasis band 10 away from the vascular access site. The compression element 16 further includes a marker 28 located thereon (e.g., approximately in the center of the main balloon 18), which permits the clinician to align the balloons 18, 20 over the center of the vascular access site.

In this embodiment, the compression element 16 is fluidly connected to the inflation port assembly 24, which includes a flexible tube 30, a bulb 32, and a tubular connector 34 containing a check valve assembly. The flexible tube 30 enters an interior of the main balloon 18 at one end thereof, and is connected to the bulb 32 at the other end thereof. The bulb 32 is subsequently connected to the tubular connector 34. Inflation of the balloons 18, 20 is achieved by inserting the protruding tip of an inflation device 80 (such as a syringe, shown in FIG. 3) into the tubular connector 34 and pushing a plunger on the inflation device 80 so as to introduce fluid (e.g., air) within the inflation device 80 through the inflation port assembly 24 into the balloons 18, 20. Once fluid has been injected into the balloons 18,20 and the protruding tip of the inflation device 80 is withdrawn from the tubular connector 34, the check valve located within the tubular connector 34 closes, preventing the fluid from leaking out and thus maintaining the balloons 18,20 in an inflated state.

Accordingly, during a radial interventional procedure, a user (such as a clinician or other health care provider) aligns the marker 28 proximate to the access site, and secures the main body 12 around the patient's wrist with the fastener 22 (which comprises two parts, not separately labeled). Once the main body 12 is secured, the user inflates the compression element 16 with a volume of fluid (e.g., 10-15 milliliters (mL) of air, 15-18 mL of air, or another initial volume). The user then performs a titration process by removing small volumes of air from the compression element 16 over time, adjusting the total volume within the compression element 16, until hemostasis is achieved and maintained while the artery or vein remains patent. After a recovery time, the clinician slowly removes volumes of air on a timed basis (such as 1 mL every fifteen minutes), observing for re-bleeds after each removal, in order to reduce the degree of access site pressure while still maintaining hemostasis. This process continues until the clinician determines that hemostasis has been achieved, at which point the hemostasis band 10 is removed from the patient's wrist.

While the hemostasis band 10 and other known hemostasis bands can achieve patent hemostasis, these devices have their drawbacks. For example, because fluid injection into the compression element 16 is based on general, recommended fluid volumes, known hemostasis bands (e.g., the TR Band) experience compression variability due to patient individuality. Factors such as patient anatomy (e.g., wrist circumference, body type), physiological variables (e.g., blood pressure (MAP) or activated clotting time (ACT) based on heparin or other anticoagulant dosages received by the patient during the vascular access procedure), variable band tensioning, and/or band materials can affect the best choice of pressure at the access site to maintain hemostasis, patency, and patient comfort. By not accounting for these factors, prior art methods of using hemostasis devices present challenges that can lead to patient discomfort, re-bleeds, long-term vascular occlusion, and/or hematomas, among other issues.

The inventors have discovered systems and methods for overcoming the above drawbacks of prior art hemostasis devices by providing real-time feedback and/or recommendations so that clinicians can achieve a consistent compression process from patient to patient to reduce the likelihood of negative events. Generally, embodiments of the disclosure provide a hemostasis band monitoring system configured to interact with existing hemostasis bands to offer hemostasis band use guidance and monitor a state of the hemostasis band during recovery. More specifically, the hemostasis band monitoring system can monitor band tightness and/or balloon pressure, and provide feedback to a clinician based on the monitored tension and pressure, either locally or to a remote device.

Figure 2:
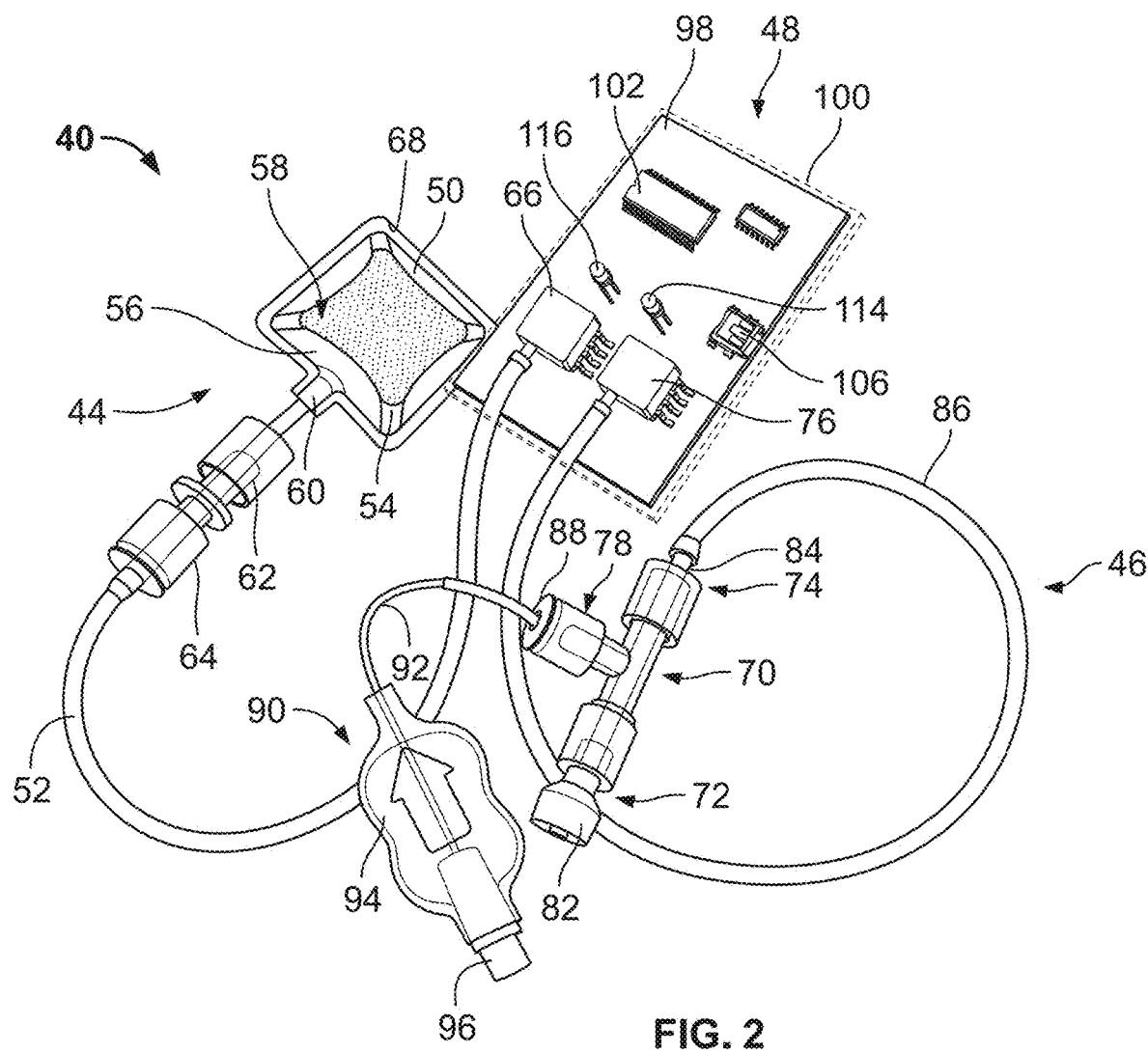
FIG. 2 is a perspective view of a hemostasis band monitoring system according to an embodiment of the present disclosure.
Figure 3:
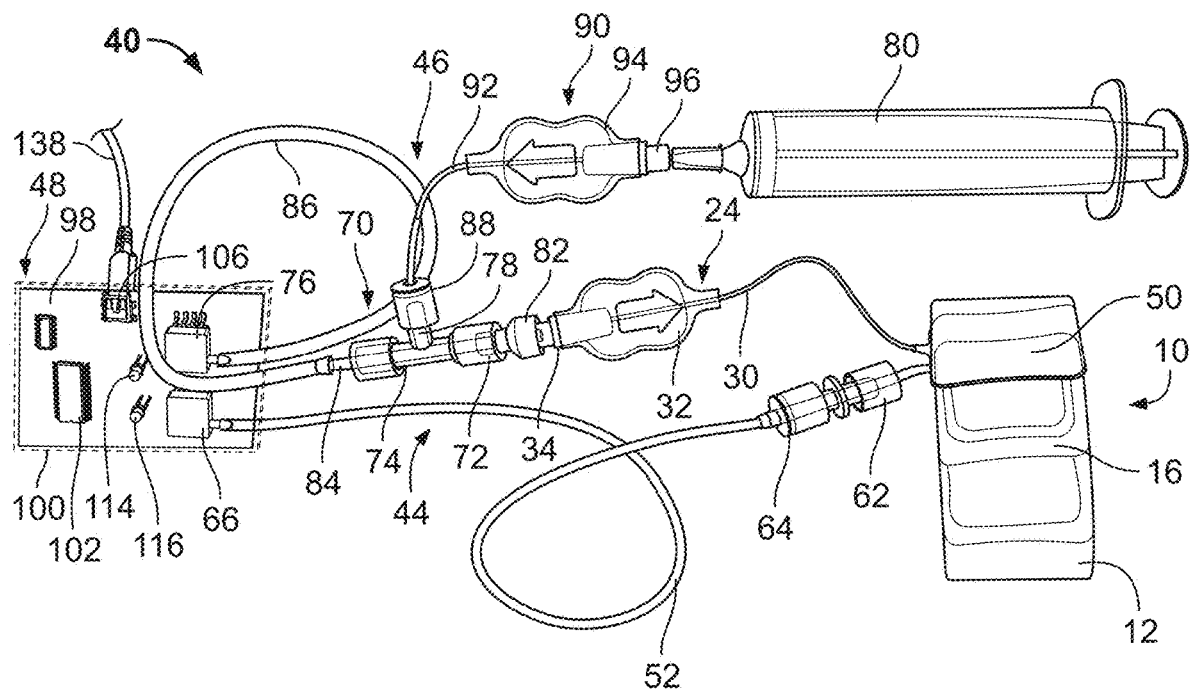
FIG. 3 is a perspective view of the hemostasis band monitoring system of FIG. 2 engaged with a hemostasis band in an as-used configuration.
Figure 4:
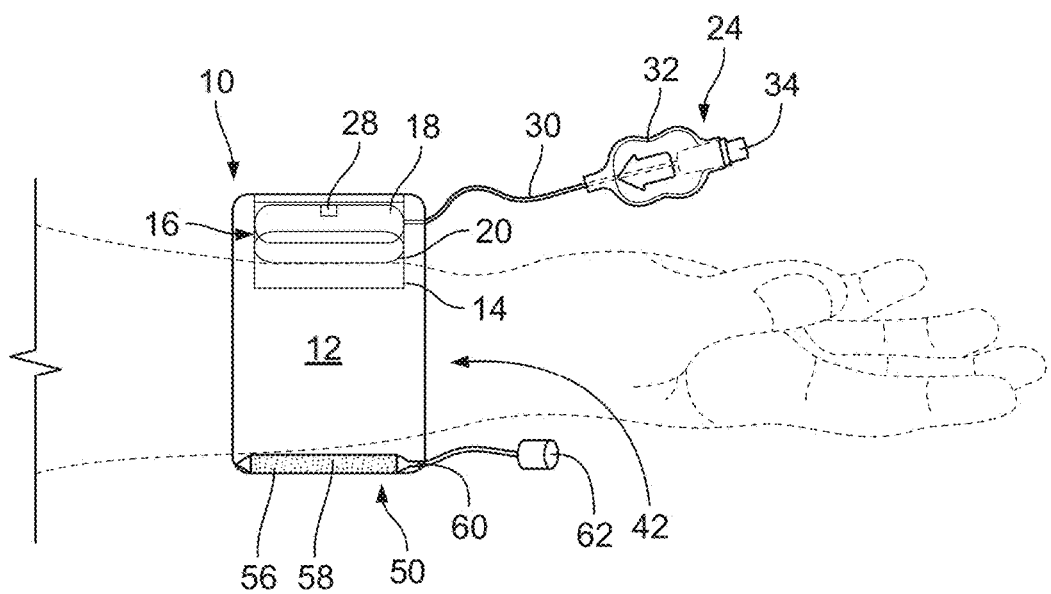
FIG. 4 is a side perspective view of a hemostasis band, shown in an as-used (e.g., fully-wrapped) configuration located around a patient's wrist, with a tension pad of the hemostasis band monitoring system of FIG. 2 shown inserted within the hemostasis band against the patient's wrist.

Various embodiments of hemostasis band monitoring systems and methods according to the present disclosure will now be described in detail. FIG. 2 shows an embodiment of a hemostasis band monitoring system 40 according to the present disclosure. In this embodiment, the hemostasis band monitoring system 40 is designed to engage with a hemostasis band (such as, for example, the hemostasis band 10 of FIG. 1), as shown in FIG. 3, where the hemostasis band 10 is configured to be wrapped and secured in place around a wrist 42 of a patient to encourage hemostasis of the radial artery, as shown in FIG. 4. Notably, when paired with a hemostasis band 10, the hemostasis band/band monitoring system combination may be considered a hemostasis device. It should further be noted that the hemostasis band monitoring systems and methods according to the present disclosure can be employed with hemostasis devices that are either specially adapted for use on other parts of a person's anatomy or with general use hemostasis devices that may be employed on various portions of a person's anatomy.

As shown in FIG. 2, the hemostasis band monitoring system 40 comprises a band tension monitoring component 44, a balloon pressure monitoring component 46, and a monitoring unit 48 in communication with the band tension monitoring component 44 and the balloon pressure monitoring component 46. Generally, the band tension monitoring component 44 is configured to engage with the hemostasis band 10 to facilitate determining a measurement indicative of band tightness when the hemostasis band 10 is secured to a patient's wrist 42. The balloon pressure monitoring component 46 is configured to engage the hemostasis band 10 to facilitate determining a measurement indicative of a pressure applied at the access site when the hemostasis band 10 is secured to the patient's wrist 42. Finally, the monitoring unit 48 is configured to communicate with the band tension monitoring component 44 and the balloon pressure monitoring component 46 to measure the respective tension and pressure, record measurement data, and communicate with a user.

The band tension monitoring component 44 is configured to provide pressure feedback to the monitoring unit 48 when the hemostasis band 10 is secured to a patient's wrist 42, via mechanical, electrical, electromechanical, volumetric, pneumatic, and/or other types of pressure sensing mechanisms. For example, in the present embodiment, the band tension monitoring component 44 comprises a tension pad 50 and a fluid communication line 52. As shown in FIG. 2, the tension pad 50 comprises a body 54 having an internal cavity 56 filled with filler material 58, and a fluid port 60 fluidly connected to the internal cavity 56. The fluid communication line 52 is removably coupled to the fluid port 60 at one end thereof via connectors 62,64, and to a pressure sensor 66 housed within the monitoring unit 48 at another end thereof, so as to fluidly couple an interior volume of the internal cavity 56 to the pressure sensor 66. The band tension monitoring component 44 in this embodiment, therefore, acts as a volumetric pressure sensing mechanism.

In use, the tension pad 50 can be positioned along the interior surface 26 of the main body 12 of the hemostasis band 10. For example, as best shown in FIG. 4, the tension pad 50 can be positioned along the interior surface 26 at a location generally opposite the compression element 16 so as to contact the patient's wrist 42 but not interfere with the compression element 16 when the hemostasis band 10 is attached thereto. Furthermore, in some embodiments, the tension pad 50 can be positioned so as to lay substantially flat against the patient's wrist 42 (e.g., so as not to wrap around the wrist 42) at a location substantially opposite the access site when the hemostasis band 10 is attached thereto. Thus, in use, the tension pad 50 can be positioned relative to the hemostasis band 10 and then the combined assembly positioned around and secured to the patient's wrist 42. Alternatively, the tension pad 50 can be positioned relative to the patient's wrist 42 and held in place while the hemostasis band 10 is positioned around the patient's wrist 42 and the tension pad 50, and then secured to the patient's wrist 42.

Accordingly, when the hemostasis band 10 is tightened around the patient's wrist 42, the tension pad 50 is compressed between the hemostasis band 10 and the patient's wrist 42, causing a change in the interior volume of the internal cavity 56 since fluid is forced out of the internal cavity 56 of the tension pad 50. Since the internal cavity 56 is fluidly connected to the pressure sensor 66 via the fluid communication line 52, this change in interior volume causes a pressure change that is detected by the pressure sensor 66. The detected pressure change can then be interpreted as a measurement of hemostasis band tension (i.e., tightness).

In some embodiments, the tension pad 50 (e.g., the body 54) and/or the hemostasis band 10 may include one or more markers (not shown) to assist in properly positioning the tension pad 50 along the hemostasis band 10. Alternatively, in some embodiments, the tension pad 50 may be equipped with a fastener (not shown) to couple the tension pad 50 to the main body 12 of the hemostasis band 10, to assist in properly positioning the tension pad 50 as well as facilitate wrapping the hemostasis band 10 around the patient's wrist 42 with the tension pad 50 in place. In some embodiments, the fastener on the tension pad 50 may be an adhesive pad configured for repeated attachment and detachment to hemostasis bands 10. In alternative embodiments, the fastener on the tension pad 50 can be any suitable type of fastener, for example hook-and-loop, snaps, buttons, laces, zippers, or hook-and-eyelet combinations, that is configured to engage with a complementary fastener located on the hemostasis band 10.

Referring back to the embodiment of FIG. 2, the body 54 of the tension pad 50 can be substantially flat and square or rectangular in cross-sectional shape, with a width that is substantially equal to or less than a width of a conventional hemostasis band 10. The body 54 can also include a length that is small enough so that the tension pad 50 can lie flat against the patient's wrist 42 when the hemostasis band 10 is attached thereto. However, in alternative embodiments, the body 54 may include a length such that the tension pad 50 at least partially wraps around the patient's wrist 42. Furthermore, in alternative embodiments, the body 54 can be circular, oval, or take on other shapes.

In this embodiment, the body 54 can be formed from material similar to that of the hemostasis band 10, such as polyvinyl chloride (PVC). For example, the body 54 can be formed from top and bottom layers of material connected to each other entirely along a perimeter 68 thereof, except for a region that forms the fluid port 60. In this manner, the internal cavity 56 is formed inside the perimeter 68 and between the top and bottom material layers. Furthermore, in some embodiments the body 54 can be formed from transparent materials, like the hemostasis band 10, or from opaque or semi-opaque materials.

Furthermore, the filler material 58 can substantially fill the internal cavity 56 of the tension pad 50. The filler material 58 can comprise a spring-like, compressible material configured to press outward when the tension pad 50 is in an uncompressed state. As a result, the filler material 58 can set a base interior volume of the internal cavity 56 when uncompressed. However, when the tension pad 50 is compressed, i.e., when the hemostasis band 10 is tightened around a wrist, the filler material 58 can compress so that the interior volume is altered based on the pad compression. Furthermore, the spring-like characteristics permit the filler material 58 to spring back to its base shape when uncompressed, yet not provide so much expansion force against the tension pad 50 so as to substantially affect tensioning of the hemostasis band 10 during use. In one embodiment, the filler material 58 can comprise a foam block. In alternative embodiments, the filler material 58 can comprise a plurality of foam blocks, a plurality of foam beads or particles, or other suitable material(s).

In this embodiment, the tension pad 50 further comprises the fluid port 60 that provides access to the internal cavity 56. The fluid port 60 extends from the body 54 of the tension pad 50 and includes a connector 62 coupled to an end thereof. The connector 62 can further be removably connected to a connector 64 of the fluid communication line 52 to couple the band tension monitoring component 44 to the monitoring unit 48. The connectors 62,64 can be, for example, mating Luer-lock connectors or any other suitable type of fluid connectors. This detachable connection between the tension pad 50 and the monitoring unit 48 can permit easy placement of the tension pad 50 and/or application of the hemostasis band 10 without being connected to the monitoring unit 48, as shown in FIG. 4. For example, a clinician may first secure the hemostasis band 10 and tension pad 50 together, and then couple the tension pad 50 to the monitoring unit 48. Alternatively, however, the clinician may first couple the tension pad 50 to the monitoring unit 48 before positioning or securing the tension pad 50 relative to the hemostasis band 10. Either way, the tension pad 50 must be connected in fluid-flow communication to the monitoring unit 48 before the hemostasis band 10 is attached to the patient, or else the tension pad 50 will already be compressed and there will be no ability to measure a volumetric differential of the tension pad 50 during tightening of the hemostasis band 10. Once the tension pad 50 is coupled to the monitoring unit 48, the band tension monitoring component 44 may be ready for use. Furthermore, this detachable connection between the tension pad 50 and the monitoring unit 48 can permit reusing the monitoring unit 48 with different tension pads 50. In yet further alternative embodiments, the band tension monitoring component 44 may not include the connectors and, rather, the fluid communication line 52 can be integrally coupled to the fluid port 60.

As noted above, the fluid communication line 52 can be coupled to the fluid port 60 at one end thereof (e.g., via the connectors 62,64), and then coupled to the pressure sensor 66 located in the monitoring unit 48 (e.g., via a friction fit) at the other end thereof. In the present embodiment, the fluid communication line 52 can comprise flexible plastic tubing. In alternative embodiments, the fluid communication line 52 can comprise multiple sections of flexible and/or rigid plastic tubing coupled together. For example, in one alternative embodiment, the fluid communication line 52 can comprise a first section of flexible or rigid plastic tubing connected to the pressure sensor 66 and extending out of the monitoring unit 48, and a second section of flexible plastic tubing removably coupled to the first section (e.g., via a suitable connector, a friction fit, or another suitable coupling) and then further coupled to the fluid port 60.

While the band tension monitoring component 44 has been shown and described herein as a volumetric pressure sensing mechanism that is fluidly coupled to the pressure sensor 66 at the monitoring unit 48, as noted above, other embodiments may include different types of pressure sensing mechanisms that may be fluidly or electrically coupled to the monitoring unit 48. For example, in one alternative embodiment, the band tension monitoring component 44 can include an electronic pressure sensor (such as a thin film pressure sensor) positioned along the main body 12 and directly coupled to a controller 102 of the monitoring unit 48. In yet another example, the balloon pressure monitoring component 46 may be used instead of, i.e., as a proxy for, the band tension monitoring component 44 to provide feedback to the monitoring unit 48 indicative of band tension.

In the present embodiment, the balloon pressure monitoring component 46 comprises a three-way connector 70 having a first port 72 configured to be coupled to the hemostasis band 10, a second port 74 configured to be coupled to a pressure sensor 76 housed in the monitoring unit 48, and a third port 78 configured to be coupled to an inflation device 80 (such as the syringe shown in FIG. 3). During conventional use of a hemostasis band 10, the inflation device 80 is connected directly to the inflation port assembly 24 in order to inflate the compression element 16. In the present embodiment, the balloon pressure monitoring component 46 can be positioned between the inflation device 80 and the inflation port assembly 24 in order to fluidly connect the balloons 18,20 of the compression element 16 to the pressure sensor 76.

In this embodiment, the first port 72 can be fluidly coupled to the hemostasis band 10. More specifically, the first port 72 can include a connector 82 adapted to connect to the tubular connector 34 of the inflation port assembly 24 (and open the check valve component of the inflation port assembly 24 when connected). The second port 74 can be fluidly coupled to the pressure sensor 76 within the monitoring unit 48. For example, the second port 74 can include a connector 84 and a fluid communication line 86 (e.g., plastic tubing) that can be coupled to the connector 84 at one end thereof, and coupled to the pressure sensor 76 at another end thereof. In one embodiment, the fluid communication line 86 can be coupled to the connector 84 and/or the pressure sensor 76 by a friction fit. Finally, the third port 78 can be fluidly coupled to the inflation device 80. For example, the third port 78 can include a connector 88 coupled to a secondary inflation port assembly 90. The secondary inflation port assembly 90, like the inflation port assembly 24 of the hemostasis band 10 described above, can include a flexible tube 92, a bulb 94, and a tubular connector 96 including a check valve assembly. The flexible tube 92 is coupled to the connector 88 at one end thereof, and is connected to the bulb 94 and, subsequently, to the tubular connector 96 at the other end thereof.

Inflation of the compression element 16 is therefore achieved by inserting the protruding tip of the inflation device 80 into the tubular connector 96, as shown in FIG. 3, and pushing a plunger on the inflation device 80, so as to introduce fluid (e.g., air) within the inflation device 80 through the secondary inflation port assembly 90, into the three-way connector 70 via the third port 78, and subsequently to the primary inflation port assembly 24 of the hemostasis band 10 via the first port 72. Once fluid has entered the hemostasis band inflation port assembly 24, inflation of the compression element 16 is achieved as described above. Once fluid has been injected into the balloons 18,20, the protruding tip of the inflation device 80 can be withdrawn from the tubular connector 96, and the check valve (not shown) located within the tubular connector 96 closes, preventing the fluid from leaking out of the secondary inflation port assembly 90.

Accordingly, with this arrangement, an interior volume of the balloons 18,20 of the compression element 16 can be fluidly connected to the pressure sensor 76. As a result, when the hemostasis band 10 is deployed, changes in the interior volume (e.g., caused by inflation, deflation, band adjustment, etc.) cause a pressure change observed by the pressure sensor 76. In turn, the observed pressure change can be interpreted as a measurement of compressive force against the access site by the hemostasis band 10. Further, when fluid is introduced into the three-way connector 70, some of this fluid travels through second port 74, connector 84, and fluid communication line 86 and is detected by pressure sensor 76, which causes the monitoring unit 48 to begin collecting data via the pressure sensor 76. In the alternative, the monitoring unit 48 may begin to collect data via the pressure sensor at some earlier time, based on human input.

As noted above, in some embodiments of a hemostasis band 10 according to the present disclosure, and in some potential applications thereof, the balloon pressure monitoring component 46 can act as a proxy for the band tension monitoring component 44. That is, under certain circumstances, data collected from the balloon pressure monitoring component 46 can be analyzed to determine measurements indicative of resulting band tightness, without the need for a separate band tension monitoring component 44. For example, if proper application of the band to a patient's body part and the approximate, resulting band tightness are assumed, collected internal balloon pressure data may be enough to provide appropriate estimates of the amount of pressure being applied by the hemostasis band 10 to the access site. Thus, in such embodiments, the band monitoring system 40 may include only the balloon pressure monitoring component 46.

The monitoring unit 48 can house the pressure sensors 66, 76 and other electronics of the band monitoring system 40, analyze data from the pressure sensors 66, 76 to determine band tension and balloon pressure, communicate such information to a user, and receive feedback or patient information from the user. For example, the monitoring unit 48 can include a control board 98 (shown in FIGS. 2, 3, and 6) that is enclosed by a housing 100 (shown in FIGS. 5-8).

Figure 8:
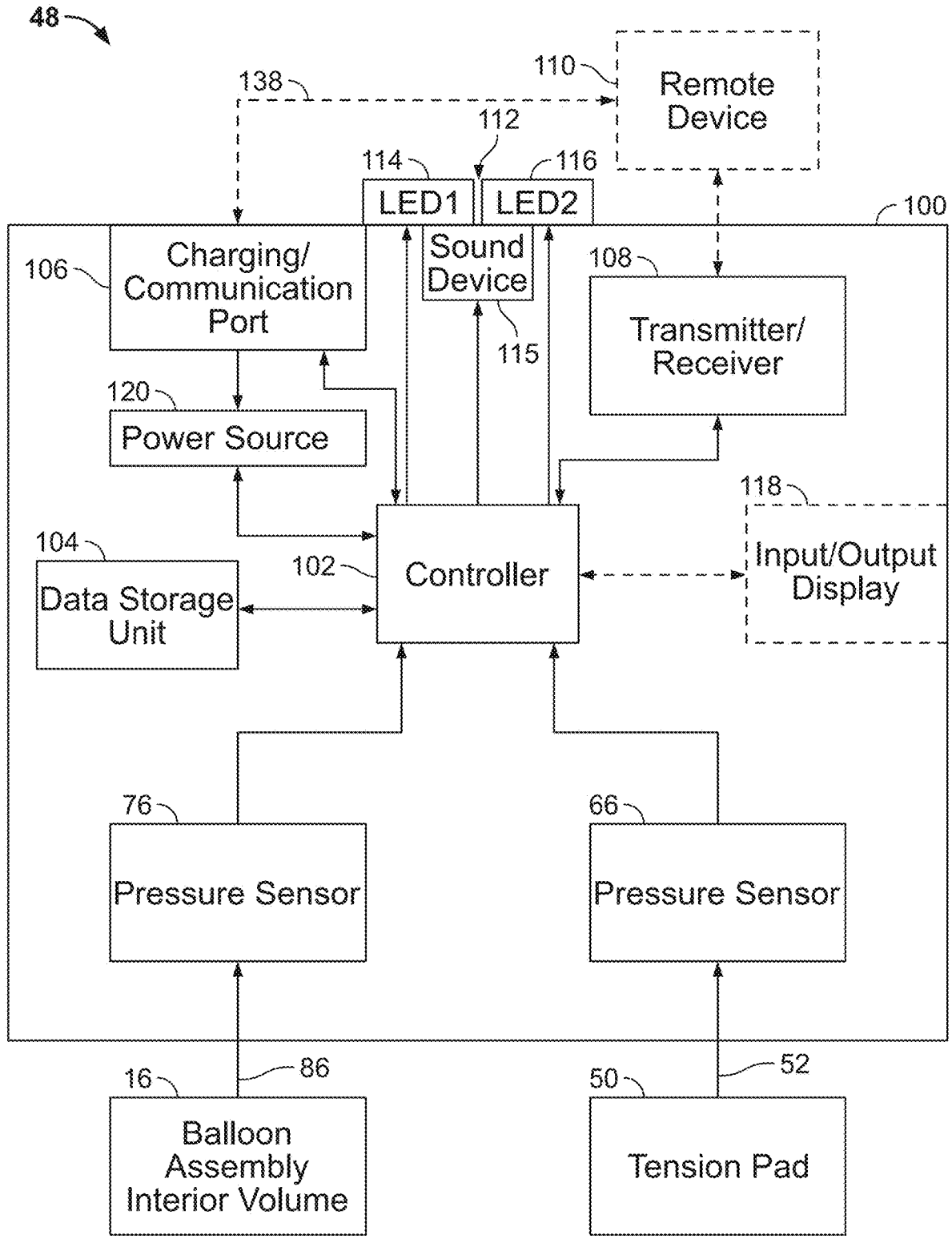
FIG. 8 is a schematic representation of a hemostasis band monitoring system, according to one embodiment of the disclosure.

FIG. 8 illustrates a schematic representation of the monitoring unit 48 according to one embodiment of this disclosure. As shown in FIG. 8, in this embodiment the monitoring unit 48 can include the housing 100, a controller 102, a data storage unit 104, a charging/communication port 106, a transmitter/receiver 108 that is, for example, configured to communicate with a remote device 110, a communication interface 112 including two LEDs 114,116 and/or a sound device 115, an optional input/output display 118 (which can display one or more graphical user interface(s) and either replace or augment the LEDs 114,116 and/or sound device 115 as a status output tool or supplemental communication interface), the tension component pressure sensor 66, the pressure component pressure sensor 76, and a power source 120 that powers the monitoring unit 48 (and which may be rechargeable via charging/communication port 106, or could comprise one or more replaceable batteries).

Generally, the housing 100 can house and protect electronics of the monitoring unit 48, which may be mounted on the control board 98 (e.g., a printed circuit board). The controller 102 can control operations of the band monitoring system 40, such as monitoring and analyzing band tension and balloon pressure, communicating such data or other information to a user, and/or receiving inputs from a user. The data storage unit 104 can store data, such as sensor data, inputted patient data or typical patient population data, or other information, as well as processes to be executed by the controller 102. The charging/communication port 106 can facilitate wired communication between the monitoring unit 48 and the remote device 110 and/or charging of the monitoring unit 48 (though in alternative embodiments these two features can be provided via separate ports). The transmitter/receiver 108 can facilitate wireless communication between the monitoring unit 48 and the remote device 110 (e.g., a standalone monitoring system, a smartphone, a tablet, or a laptop). The communication interface 112 can communicate information to a user, for example, via the LEDs 114,116 that extend through the housing 100 and/or via the sound device 115, which can be configured to emit an audible alert (such as a beep, tone, chime, or alarm). As noted above, the tension component pressure sensor 66 can sense a measurement indicative of band tightness. The pressure component pressure sensor 76 can sense a measurement indicative of pressure against an access site.

In this embodiment, as shown in FIGS. 5 and 6, the housing 100 can comprise an upper housing 122 and a lower housing 124 coupled together, such as by fasteners, snap-fit connection, or other suitable coupling methods. The housing 100 can define a first aperture 126 sized to provide access to the charging/communication port 106 on the control board 98, a second aperture 128 and a third aperture 130, each of which is sized to receive a respective one of the fluid communication lines 52,86 therethrough, and a fourth aperture 132 and a fifth aperture 134, each of which is sized to permit a respective one of the first and second LEDs 114,116 to extend therethrough. In some embodiments, the housing 100 can further include additional apertures, such as for the input/output display 118 (shown in FIG. 7) or other ports or communication mechanisms. In some embodiments, the housing 100 can include a connection point between the upper and lower housings 122,124 and/or one or more of the apertures 126,128,130,132,134, can include seals or coverings (not shown) to ensure that the housing 100 is substantially water resistant in order to protect the electronics housed therein from liquids and/or other contaminants.

Figure 7:
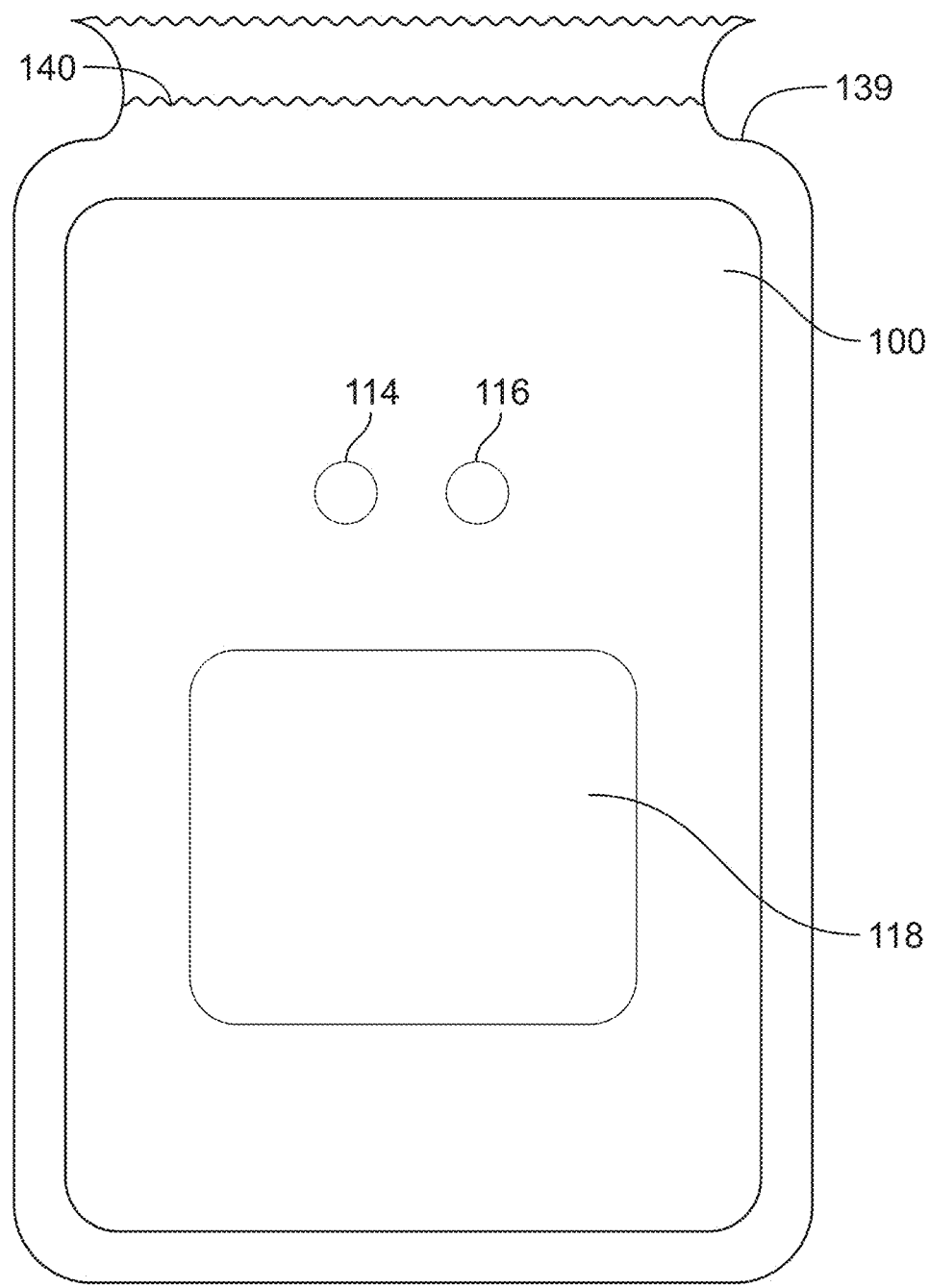
FIG. 7 is a top view of an alternative embodiment of a monitoring unit of the hemostasis band monitoring system of FIG. 2.

Furthermore, in some embodiments, as shown in FIG. 7, the monitoring unit 48 can include a covering 139 wrapped around the housing 100. The covering 139 can be disposable and used to provide a temporary sterile barrier, permitting use of the monitoring unit 48 in sterile environments (e.g., operating rooms or other environments). For example, the covering 139 can be wrapped or secured around the housing 100 while still permitting fluid connections from the fluid communication lines 52, 86 therethrough. When a sterile environment is no longer necessary (e.g., once the patient is in recovery, outside of the operating room), the covering 139 may be removed and disposed. In one embodiment, the covering 139 can be a flexible plastic covering that is transparent so that the LEDs 114, 116 or other input/output display 118 can still be viewed and/or interacted with in the sterile environment. In some embodiments, the covering 139 may be provided with one or more elastic or adhesive element(s) 140 that allow for the covering 139 to be substantially sealed around the housing 100 and/or any fluid communication lines 52, 86, thus improving the performance of the covering 139 as a sterile barrier.

Figure 9:
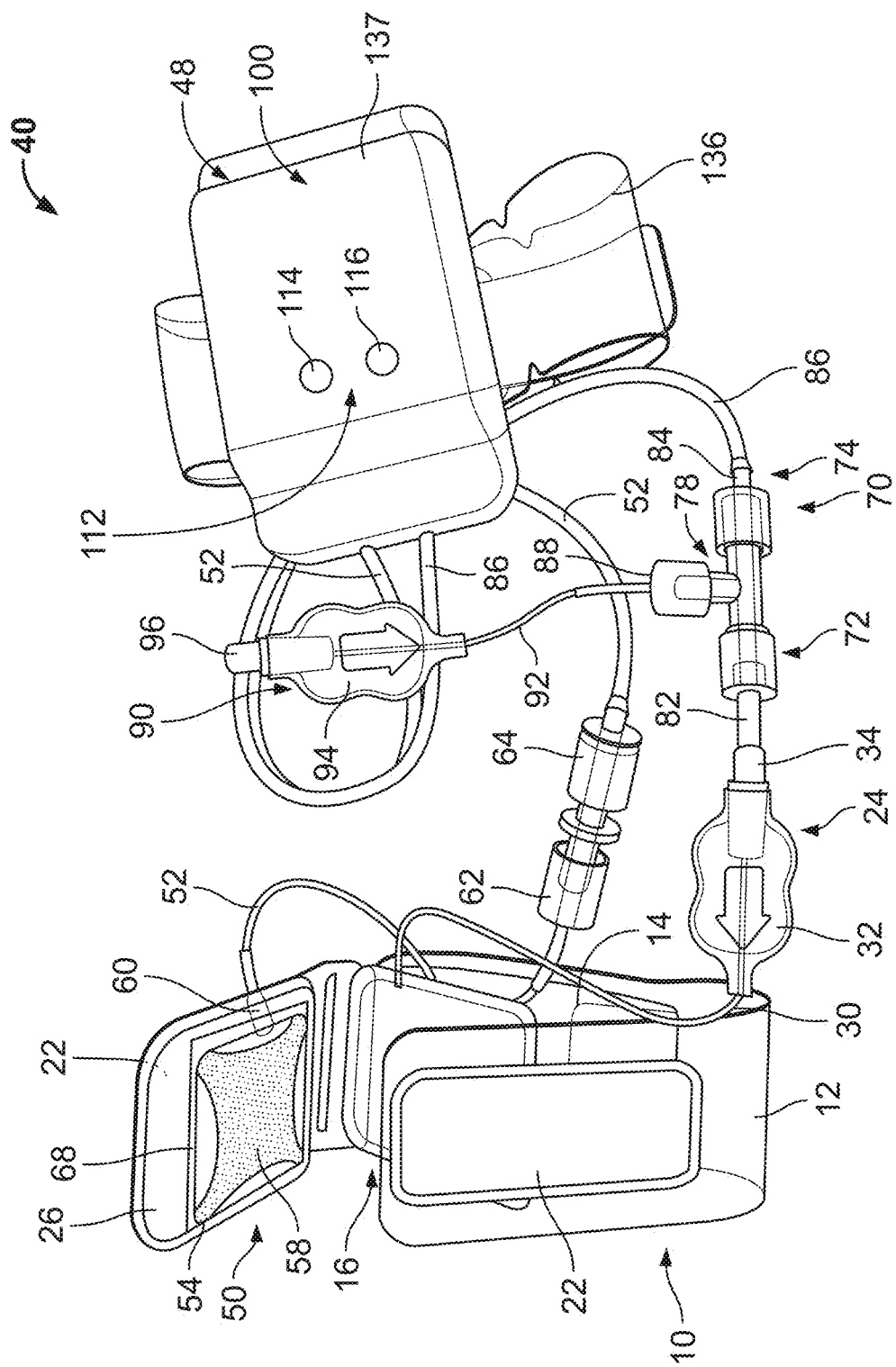
FIG. 9 is a perspective view of a hemostasis band monitoring system, according to one embodiment of the disclosure, engaged with a hemostasis band in an unwrapped configuration.

Additionally, in some embodiments, as shown in FIG. 9, the housing 100 can include a strap 136 coupled to an outer surface 137 thereof. The strap 136 can be adjustably sized to fit around a circumference of a patient's limb and, thus, can be substantially similar in total length to a length of the main body 12 of the hemostasis band 10. Furthermore, the strap 136 can include one or more fasteners (such as complementary patches of hook-and-loop type fasteners (e.g., Velcro®), snaps, buttons, laces, zippers, or hook-and-eyelet combinations, or other suitable fasteners) configured to secure the strap 136 to itself around the patient's limb. In this manner, the housing 100 becomes a wearable device, which may assist with patient comfort and mobility and prevent unwanted malfunction of the monitoring unit 48. In alternative embodiments, the strap 136 can instead comprise multiple straps configured to be removably coupled to each other to secure the housing 100 to the patient. Accordingly, in this embodiment the monitoring unit 48 is a small, portable, and/or wearable device.

The controller 102 can provide data processing capabilities. In this embodiment, the controller 102 can include one or more microcontrollers mounted on the control board 98. The controller 102 can further be in communication with one or more components of the monitoring unit 48, such as the data storage unit 104, the charging/communication port 106, the transmitter/receiver 108, the communication interface 112, the (optional) input/output display 118, the tension component pressure sensor 66, the pressure component pressure sensor 76, and/or the power source 120. Generally, the controller 102 can operate in conjunction with these components to record measurements indicative of band tightness and balloon pressure, locally store these measurements, analyze the measurements (e.g., compare them against expected values for the individual or a population of individuals with similar physiologic attributes), communicate the measurements, alerts, and/or reports to one or more users locally and/or remotely, and/or receive information (such as feedback or other patient information) locally and/or remotely.

For example, in the present embodiment, the data storage unit 104 can serve as local memory for the monitoring unit 48 and store the firmware that manages the operation of the monitoring unit hardware, including programs and/or algorithms for execution by the controller 102. Furthermore, the controller 102 can store raw data from the sensors 66,76, processed measurements, analyses, patient information, and/or other information locally via the data storage unit 104. In one example, the controller 102 can store a session log of a recovery procedure-including periodic band tension and balloon pressure measurements-a log of alerts communicated to the user, user feedback, and/or other information. Furthermore, the controller 102 can store acceptable or expected patient parameters, for example those parameters that have been inputted by the clinician, to be used during the recovery procedure. The controller 102 can also store one or more of the following: algorithms for determining optimal band tightness and/or balloon pressure for the particular recovery procedure based on the patient parameters; algorithms to learn from the session logs and user feedback to continuously update the algorithms for determining optimal band tightness and/or balloon pressure; processes for communicating alerts or instructions to the user; and/or other algorithms or processes.

While the monitoring unit 48 can locally store information via the data storage unit 104, the monitoring unit 48 can further communicate information to, or receive information from, one or more remote devices 110 via the charging/communication port 106 and/or the transmitter/receiver 108. In particular, the charging/communication port 106 can facilitate wired communication between the monitoring unit 48 and the remote device 110. In this embodiment, the charging/communication port can be a USB port mounted on the control board 98. Accordingly, the remote device 110 can be connected to the monitoring unit 48 via a USB connector cable 138 plugged into the USB port, as shown in FIGS. 3 and 8. In addition to facilitating communication between the remote device 110 and the monitoring unit 48, the USB connector cable 138 can be alternately connected to an external power source (not shown) in order to charge the power source 120 of the monitoring unit 48. However, in alternative embodiments, the charging/communication port can be another suitable data connection and/or power transfer port, or these two functions could be accomplished via separate ports.

The transmitter/receiver 108 can facilitate wireless communication between the monitoring unit 48 and the remote device 110. For example, the transmitter/receiver 108 can comprise a wireless communication module configured to communicate to a remote device 110 via cellular, WiFi, Bluetooth, or other wireless transmission protocols.

Accordingly, the monitoring unit 48 can be configured to communicate in real-time and/or retrospectively, wired and/or wirelessly, with a remote device 110. In some embodiments, a remote device 110 can be, but is not limited to, an external computer, a tablet, a mobile device, a wearable device, or another suitable device. Through the above wired or wireless communication components, the remote device 110 can receive patient data, alerts, and/or instructions from the monitoring unit 48, communicate patient information to the monitoring unit 48, and/or provide visual, audio, and/or tactile feedback to the user, for example via an application (e.g., a mobile medical application), as further described below. Such feedback may relate to patient data, status alerts, and/or instructions, power source status or performance, or other types of feedback. In one example of a mode of operation, the application queries the user for patient data (e.g., BMI, MAP, ACT, titration volume, and/or blood pressure changes over time) and provides visual feedback to the user during a hemostasis procedure to communicate to the user whether the hemostasis band 10 is being applied with an expected or optimal tension and/or whether the compression element 16 is applying an expected or optimal pressure to the access site over the course of the hemostasis procedure. Additionally, in some embodiments, the remote device 110 may take the place of or augment the on-board communications interface 112.

While the remote device 110 can communicate feedback to the user while located remote from the monitoring unit 48, the communication interface 112 can also communicate information to a user locally. In this embodiment, the communication interface 112 includes the two LEDs 114, 116, which may be, for example, a green LED 114 and a red LED 116. In one example, the controller 102 can illuminate the green LED 114 when the hemostasis band 10 is properly tightened, sufficient balloon pressure is provided, and/or the recovery procedure is proceeding in an expected or optimal manner. In contrast, the controller 102 can illuminate the red LED 116 when the hemostasis band 10 is insufficiently tightened, the balloon pressure is insufficient, and/or the recovery procedure is not proceeding in an expected or optimal manner. In some embodiments, the controller 102 can illuminate the LEDs 114,116 in a constant or flashing manner in order to communicate different information. Additionally, in alternative embodiments, the communication interface 112 may include multiple green, red, and/or other colored LEDs, or multi-colored LEDs, to communicate information to the user. Furthermore, the communication interface 112 includes a sound device 115 that can emit audible alerts. In one example, the controller 102 can, via the sound device 115, emit a beep or other sound in a first manner when the hemostasis band 10 is properly tightened, sufficient balloon pressure is provided, and/or the recovery procedure is proceeding in an expected or optimal manner. In contrast, the controller 102 can, via the sound device 115, emit a beep or other sound in a second manner when the hemostasis band 10 is insufficiently tightened, the balloon pressure is insufficient, and/or the recovery procedure is not proceeding in an expected or optimal manner.

In some embodiments, in addition to or as an alternative to the communication interface 112, the monitoring unit 48 can include the input/output display 118. As shown in the monitoring unit 48 of FIG. 7, the input/output display 118 can be, for example, a screen capable of communicating information to a user (such as via a graphical user interface (GUI)), a touch screen capable of receiving inputs from the user, or both. Thus, in such embodiments, the input/output display 118 can communicate information to a user locally, in addition to or in place of the communication interface 112. The input/output display 118 can also receive inputs from the user locally, in addition to or in place of the application on the remote device 110. When used in place of the remote device 110, the band monitoring system 40 can be completely self-contained to assist recovery procedures. Accordingly, any communication between the remote device 110 and the controller 102 described herein can instead be replaced with communication between the input/output display 118 and the controller 102. In alternative embodiments, the monitoring unit 48 may not be equipped with any on-board output device (e.g., communication interface 112 or input/output display 118), and all information may be communicated to the user solely via wired and/or wireless communication means to an external device (e.g., remote device 110).

As noted above, in the present embodiment, the monitoring unit 48 includes the pressure sensors 66, 76 configured to monitor band tension and balloon pressure, respectively. As shown in FIGS. 2 and 3, the pressure sensors 66, 76 may be mounted on the control board 98 and oriented toward the apertures 128, 130 to facilitate connection with the respective fluid communication lines 52, 86. In alternative embodiments, the monitoring unit 48 can include additional inputs for other sensors such as, but not limited to, a blood sensor (e.g., to monitor re-bleeds), a temperature sensor, a patient movement sensor, and/or a local patency sensor (e.g., using ultrasound or a suitable equivalent).

Finally, in this embodiment, the power source 120 can power the monitoring unit 48, which may be a battery housed within the housing 100 on the control board 98, as shown in FIG. 6. More specifically, the controller 102 and/or one or more other components of the monitoring unit 48 can be connected to the power source 120 in order to power the monitoring unit 48. In some embodiments, the battery may be rechargeable, for example, via the charging/communication port 106. For example, in this embodiment, the battery may be a rechargeable lithium ion battery. In alternative embodiments, the battery may be replaceable. For example, the housing 100, or a portion thereof, can be configured to provide access to the battery for replacement. Additionally, in some embodiments, to preserve battery, the monitoring unit 48 can include an on/off button, switch, or other mechanism for turning off the band monitoring system 40 when not in use.

FIG. 10 illustrates a method 150, according to one embodiment of the disclosure, of performing a hemostatic procedure using the hemostasis band monitoring system 40 described above. Generally, known data about the patient (for example, BMI, MAP, and ACT) are inputted to the hemostasis band monitoring system 40 at step 152, the tension pad 50 of the band monitoring system 40 is positioned relative to a hemostasis band 10 and/or the patient at step 154, and the hemostasis band 10 is positioned around the patient at step 156. The hemostasis band 10 is then tightened around the patient at step 158 and the band monitoring system 40 checks whether the band tension is sufficient at step 160. If not, the band monitoring system 40 sends feedback to the user to adjust the band tension at step 162. Once band tension is sufficient, as determined at step 160, the user can begin a titration procedure to fill the internal volume of the balloons 18,20, at step 164, and the band monitoring system 40 checks whether the balloon pressure is sufficient at step 166. If not, the band monitoring system 40 sends feedback to the user to adjust the balloon pressure at step 168. Once balloon pressure is sufficient, as determined at step 166, the band monitoring system 40 monitors the band tension and balloon pressure, and records data measurements at step 170. The band monitoring system 40 continuously or periodically checks for an excessive pressure drop at step 172 and, if such a drop is observed, sends an alert to the user at step 174. If not, the band monitoring system 40 reverts back to step 170. The band monitoring system 40 also continuously or periodically checks for a band tension measurement indicative of the hemostasis band 10 being moved or taken off at step 176 and, if such a measurement is observed, sends an alert to the user at step 178. If not, the band monitoring system 40 reverts back to step 170. Furthermore, the band monitoring system 40 determines whether a "record time" has expired at step 180 or whether a user has manually stopped the session at step 182 and, if such time has expired or a user has ended the session, optionally receives feedback from the user and stores a session log of the procedure at step 184, and then ends the procedure. If not, the band monitoring system 40 reverts back to step 170, where band tension and balloon internal pressure continue to be recorded.

More specifically, at step 152, known patient data is inputted to the hemostasis band monitoring system 40, for example, through a remote device 110 or a GUI on the input/output display 118. The patient parameters can include patient physiological variables that can affect access site pressure and/or recovery time. For example, patient data can include, but is not limited to, patient body mass index (BMI), activating clotting time (ACT), and blood pressure or mean arterial pressure (MAP).

For example, patient body type can be a factor in achieving hemostasis in relation to the amount of air applied to the balloons 18,20 of the compression element 16. More specifically, very thin (i.e., low BMI) patients with superficial radial arteries can achieve radial artery closure with lower pressure applied as compared to very heavy (i.e., high BMI) patients, which would need higher pressure applied to achieve arterial closure.

Additionally, ACT can affect healing times due to the effects of clotting. For example, during a radial interventional procedure, the patient may be administered some amount of Heparin to reduce the risks of blood clots forming in the vasculature. Heparin is metabolized in the body and, given the length of its half-life, can increase the time for natural closure of the arteriotomy during the recovery procedure. Accordingly, this extended healing time may require the hemostasis band 10 to apply patent hemostatic pressure for a longer period.

Further, MAP can affect healing times and pressure requirements. For example, if a patient has high blood pressure, additional compression may be required to ensure hemostasis, which translates to requiring a higher balloon pressure of the hemostasis band 10.

Furthermore, the materials of the hemostasis band 10 (e.g., thin layers of PVC) naturally relax over time, resulting in a logarithmic pressure decay after the balloons 18,20 are inflated. For example, the internal pressure can start to decay within a few minutes and drop up to 50% more within hours. As a result of this material relaxation and other variables such as BMI, ACT, MAP, and the type of vascular access procedure that has been performed, a clinician may need to apply more air over time so that the pressure decay curve maintains the desired (e.g., greater) pressure for a longer period of time. To achieve this goal, in some embodiments the hemostasis band monitoring system 40 may prompt the clinician to add air at certain intervals, either based on measured pressures or by including the known material relaxation characteristics of the hemostasis band 10 in the algorithm by which the hemostasis band monitoring system 40 operates, thus providing predictions to a clinician for when it may be necessary to add air.

In one embodiment, a series of GUI screens can be provided via the input/output display 118 (or via an application on the remote device 110) to prompt the user for one or more of the above variables. Accordingly, in this embodiment, based on the inputted patient data at step 152, the controller 102 can determine an optimal initial pressure or initial pressure range and/or pressure decay curve for the hemostasis procedure. In alternative embodiments, based on historical data collected from populations having similar measured or known characteristics (e.g., based on algorithms stored within the data storage unit 104), the controller 102 can determine what constitutes an optimal or effective pressure decay curve for that individual, and provide feedback to the clinician accordingly (e.g., with respect to an appropriate optimal initial pressure or initial pressure range). Further, in some embodiments, inputted data or historical population data—or a doctor's manual directive—can be used to determine an appropriate patient observation interval, that is, the amount of time during which data will be recorded by default, unless overridden by the clinician. This inputted or historical population data—or a doctor's manual directive—can also be used to determine how often a clinician should check a particular patient during the hemostasis procedure.

As noted above, the patient data can be inputted to the monitoring unit 48 through a remote device 110 or the input/output display 118. For example, the remote device 110 can include an application stored thereon that prompts a user for such information via a graphical user interface. In some embodiments, the application can communicate the information to the controller 102, which can then determine the optimal pressure, pressure range, and/or pressure decay curve. In alternative embodiments, the application can include algorithms for determining a customized pressure, pressure range, and/or pressure decay curve to then submit to the monitoring unit 48. Additionally, the application can further assist the user throughout the hemostasis procedure, as further described below.

Referring back to the method 150 of FIG. 10, at step 154, the user can position the tension pad 50 relative to a hemostasis band 10 and/or the patient, as described above. Next, the hemostasis band 10 is positioned around the patient at step 156, as described above (for example, by aligning the marker 28 with the access site). The hemostasis band 10 is then tightened around the patient at step 158 and the band monitoring system 40 checks whether band tension is sufficient at step 160. More specifically, the amount of air needed to facilitate hemostasis is dependent in part upon how tightly the clinician applies the hemostasis band 10 at step 158. For example, the volume of air needed to create arterial compression can more than double when a band 10 is applied loosely, as compared to a tightly secured band. By setting a threshold tension (or threshold tension range), as stored in the data storage unit 104, band tension variability can be substantially eliminated from the procedure. Accordingly, if the controller 102 determines that the monitored tension (as detected by the tension monitoring component 44) falls below the threshold tension, the band 10 is not sufficiently tensioned and the controller 102 sends feedback to the user to adjust the band tension at step 162. Since it is also desirable to avoid an overtightened band, which can cause patient discomfort, the data storage unit 104 could also store data on maximum acceptable band tension settings, and alert the clinician when these values have been exceeded.

Figure 11A:
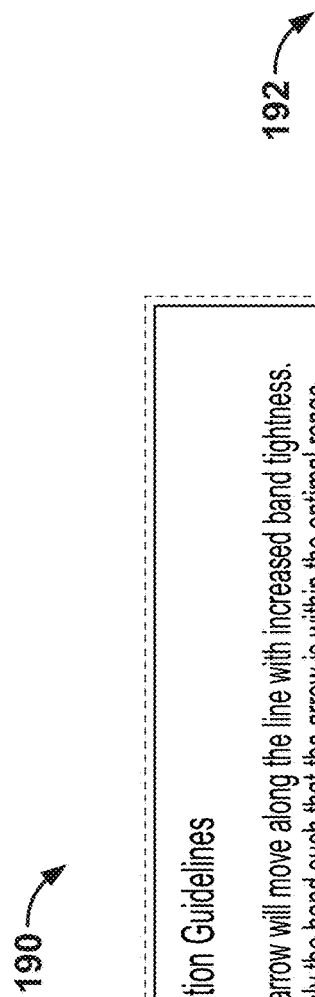
FIGS. 11A-11B are screen illustrations showing a graphical user interface of the hemostasis band monitoring system, where

The feedback can be communicated to the user via the communication interface 112 (e.g., via activating one or both LEDs 114,116 and/or the sound device 115 in a particular manner), or via the application on the remote device 110. For example, FIG. 11A illustrates an example graphical user interface 190 from an application, according to this embodiment, which provides feedback to the user with respect to band tightness. In particular, the graphical user interface 190 illustrates an arrow on a sliding meter ranging from "not tight enough" to "optimal band tightness" to "too tight." In this embodiment, the controller 102 can correlate the illustrated meter to a stored range of suitable band tensions, as programmed by a user and/or optimized by the controller 102 through user feedback, as further described below. The controller 102 can analyze the actual tension data observed by the pressure sensor 66 and, through the application, map a present band tension along the illustrated meter by "moving" the arrow accordingly. Thus, the user can refer to the location of the arrow along the meter on the graphical user interface 190 and make adjustments as necessary in order to properly secure the hemostasis band 10 to the patient within an optimal band tension range.

While the feedback in this present embodiment is shown and described as presenting to the user a moving arrow along a meter, in alternative embodiments, the feedback via the application may simply be discrete messages, such as "not tight enough," "optimal band tightness," and "too tight" readouts, red/green colors shown based on tension being inside or outside a desired range, audio or tactile communications, or other types of feedback to communicate to the user when optimal band tightness is reached. Additionally, while the graphical user interface 190 is described as being displayed via the remote device 110, in alternative embodiments, the graphical user interface 190 may be displayed via the input/output display 118.

In another example, feedback can be communicated to the user by illuminating one LED 114 (e.g., a red LED) when the hemostasis band 10 is not sufficiently tensioned and illuminating the other LED 116 (e.g., a green LED) when the hemostasis band 10 is sufficiently tensioned. In another example, one or both LEDs 114, 116 can flash when the hemostasis band 10 is not sufficiently tensioned and can provide continuous illumination when the hemostasis band 10 is sufficiently tensioned. In addition, the LEDs 114, 116 can flash at a consistent rate when the hemostasis band 10 is insufficiently tensioned or can flash at varied rates based on how close the measured tension is to an optimal tightness. In yet another example, the sound device 115 can emit an audible beep when the hemostasis band 10 is sufficiently tensioned. The sound device 115 can alternatively emit a series of beeps at a consistent rate when the hemostasis band 10 is insufficiently tensioned and then emit one long beep when the hemostasis band 10 is sufficiently tensioned. Furthermore, the sound device 115 can emit a series of beeps at a varying rates based on how close the measured tension is to an optimal tightness, then emit one long beep when the hemostasis band 10 is sufficiently tensioned. Accordingly, feedback can be presented in an analog manner (e.g., as a dial or arrow moving along a meter on the input/output display 118 or the remote device 110, varying flashing rates of LEDs 114, 116, varying beeping, etc.) or a digital manner (e.g., as discrete instructions, via the LEDs 114, 116, the sound device 115, the input/output display 118, and/or the remote device 110).

In some embodiments, the band monitoring system 40 may not include a separate tension monitoring component 44. In such embodiments, steps 160 and 162 may instead include the user visually checking for sufficient tension and/or receiving feedback directly from the patient. Furthermore, while determining sufficient band tension is described above with respect to the tension monitoring component 44, in some embodiments data may be retrieved and analyzed from the balloon pressure monitoring component 46 to determine band tension or certain variables indicative of sufficient band tension.

Once the band tension is sufficient, as determined at step 160, the user can begin the titration procedure to fill the internal volume of the balloons 18,20, at step 164, and the band monitoring system 40 checks whether the balloon pressure is sufficient at step 166. More specifically, in this embodiment, the controller 102 can monitor balloon pressure (as detected by the balloon pressure monitoring component 46) and compare the balloon pressure to the optimal pressure and/or optimal pressure decay curve determined based on the patient data inputted at step 152. If the controller 102 determines that the monitored pressure falls outside the optimal pressure or pressure decay curve, the controller 102 sends feedback to the user to adjust the balloon pressure at step 168.

Figure 11B:
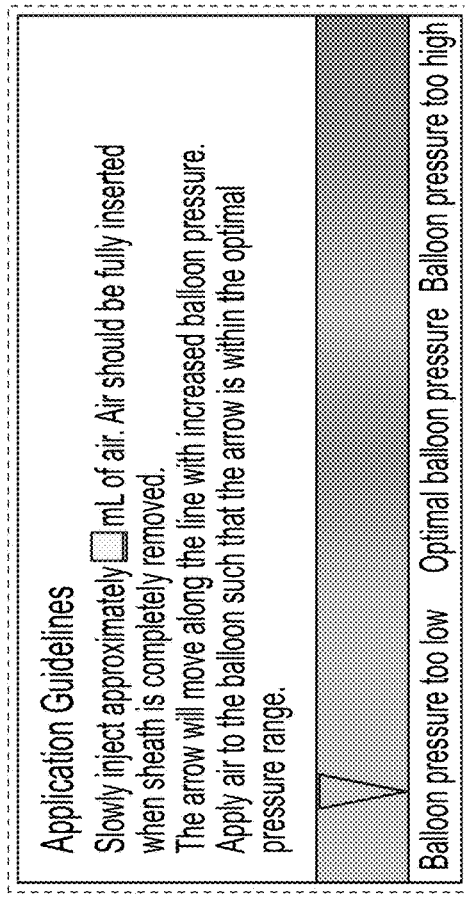

The feedback can be communicated to the user via the communication interface 112 (e.g., via activating one or both LEDs 114,116 or the sound device 115 in a particular manner), or via the application on the remote device 110. For example, FIG. 11B illustrates an example graphical user interface 192 from an application, according to this embodiment, which provides feedback to the user with respect to balloon pressure. In particular, the graphical user interface 192 illustrates an arrow on a sliding meter from "balloon pressure too low" to "optimal balloon pressure" to "balloon pressure too high." In this embodiment, the controller 102 can correlate the illustrated meter to a stored range of balloon pressures, as initially programmed by a user, updated by the controller 102 based on inputted patient data, and/or optimized by the controller 102 through user feedback, as further described below. The controller 102 can analyze the pressure data observed by the pressure sensor 76 and, through the application, map a present balloon pressure along the illustrated meter by "moving" the arrow accordingly. Thus, the user can refer to the location of the arrow along the meter on the graphical user interface 192 and make adjustments as necessary in order to properly fill the balloons 18,20 to achieve an optimal pressure range.

While the feedback in this present embodiment is shown and described as presenting to the user a sliding arrow along a meter, in alternative embodiments, the feedback via the application may simply be discrete messages such as "pressure too low," "optimal pressure," and "pressure too high" readouts, red/green colors shown based on pressure or pressure decay curves being inside or outside a desired range, audio or tactile communications, or other types of feedback to communicate to the user when optimal balloon pressure is reached. Additionally, while the graphical user interface 192 is described as being displayed via the remote device 110, in alternative embodiments, the graphical user interface 192 may be displayed via the input/output display 118.

Once balloon pressure is sufficient, as determined at step 166, a recovery period begins and the controller 102 continues to monitor the band tension and balloon pressure, as described above, and records data measurements at step 170 throughout the remainder of the hemostasis procedure. For example, the controller 102 can locally store such data in the local storage unit 104, along with an elapsed time of the recovery period. In some embodiments, the controller 102 can also communicate this monitoring operation to the user via the communication interface 112 (e.g., by emitting the green LED 114 in a constant or flashing manner) and/or to the remote device 110. For example, in one embodiment, the controller 102 can control the application on the remote device 110 to illustrate a graphical user interface (not shown) indicating that monitoring is in progress, the elapsed time, and/or one or more prompts to the user (such as a prompt to continue monitoring, a prompt to stop monitoring and download the session data, and/or a prompt to stop monitoring and delete the session data). Furthermore, in some embodiments, once balloon pressure is sufficient, the user must select a "start" prompt to continue monitoring in order to proceed to step 170.

Additionally, throughout the remainder of the hemostasis procedure, the controller 102 continuously checks for an excessive pressure drop (step 172), band removal (step 176), record time expiration (step 180), or a manual stop (step 182). If none of these actions are observed, the controller 102 reverts back to step 170 to continue monitoring band tension and balloon pressure through the remainder of the scheduled recording time period.

The controller 102 continuously or periodically checks for an excessive pressure drop at step 172 and, if such a drop is observed, sends an alert to the user at step 174. An excessive pressure drop can be a drop outside the optimal pressure, optimal pressure range, or pressure decay curve, for example, indicating a leak or improper handling of the hemostasis band 10. The alert can be provided to the user so that they can immediately check on the patient for leaks or other mishandling of the hemostasis band 10. For example, the alert can be an audible alert via the sound device 115 and/or the remote device 110, or a visual alert via the LEDs 114, 116, the input/output display 118, and/or the remote device 110.

The excess pressure drop alert can be communicated to the user via the communication interface 112 (such as by emitting the red LED 116 in a constant or flashing manner or emitting one or more beeps via the sound device 115), or via the application on the remote device 110. For example, in one embodiment, the application can display a pop-up alert to the user. Thus, the user can be immediately alerted in the event of a pressure drop so that the user can return to the patient. Without such feedback, it may be some time before the clinician checks on the patient for the next air removal and, as a result, the patient might suffer negative outcomes.

In this embodiment, the controller 102 also continuously or periodically checks, at step 176, for a band tension measurement indicative of the hemostasis band 10 being moved or taken off. The band off alert can be communicated to the user via the communication interface 112 (such as by emitting the red LED 116 in a constant or flashing manner or emitting one or more beeps via the sound device 115), or via the application on the remote device 110. For example, in one embodiment, the application can display a pop-up alert to the user. Thus, the user can be immediately alerted in the event of such a situation so that the user can return to the patient. Without such feedback, it may be some time before the clinician checks on the patient for the next air removal and, as a result, the patient might suffer negative outcomes.

While the low pressure and band off alerts are described in this embodiment, other alerts may be provided in some embodiments. For example, in alternative embodiments, a low tension alert, a high tension alert, a low pressure alert, and/or a high pressure alert may be provided to the clinician while tension and pressure are being monitored. In further embodiments, a low battery alert may be provided when the controller 102 senses that a battery level of the power source 120 is low so that the clinician can replace or charge the battery or the monitoring unit 48 before or during use.

At step 180, the band monitoring system 40 determines whether a "record time" has expired and, at step 182, the band monitoring system 40 determines whether a user has manually stopped the session. The record time can be a set time (e.g., previously inputted to the controller 102) during which the controller 102 will operate. Further, the user can stop the session via a prompt displayed through the application during monitoring, as described above. If such time is expired, or if the user stops the session, as determined at steps 180 and 182, respectively, the controller 102 can receive feedback from the user and store a session log of the procedure at step 184, and then end the procedure.

As noted above, the controller 102 can store a session log locally via the data storage unit 104. For example, the data storage unit 104 can be nonvolatile memory and data from the session can be stored throughout the procedure so that if the monitoring unit 48 loses power the data may still be available when power is again provided. Furthermore, once a procedure is completed, feedback can be received and all data related to the procedure can be packaged as a completed session log. In some embodiments, the user can have the option to transmit the session log to the remote device 110 for remote storage and/or locally delete the session log from the data storage unit 104. For example, in one embodiment, the controller 102 and the data storage unit 104 can be configured to locally store one session log at a time. As a result, if a new procedure is started, a user may be given the option to remotely transmit the previous session log (if it has not yet been transmitted) or delete the previous session log.

As noted above, a session log can include feedback from the patient and/or the user. Hospitals are increasingly rated on the quality of the patient experience. A hemostasis device firstly has to stop bleeding (i.e., achieve hemostasis), secondly not cause a long-term occlusion (i.e., maintain vascular patency), and thirdly be as comfortable as possible. The lower the pressure, the greater the comfort, but not at the cost of bleeding or secondary hematoma. Such patient feedback to the monitoring unit 48 can therefore include, but is not limited to, a rating of patient comfort (e.g., on a subjective 1-10 or 0-10 comfort scale), whether a hematoma occurred, and whether a re-blood occurred. In one example, such feedback can be gleaned from the user via one or more prompts from the application on the remote device 110 (e.g., through a graphical user interface). This data can be used by the controller 102 to improve the algorithms used to determine optimal tightness and/or pressure (including, but not limited to, adjusting weighting factors for certain variables in the algorithms). Thus, the band monitoring system 40 can be improved over time based on inputted feedback relating to patient data and hemostasis band performance.

By way of example, if patient comfort was low, the calculated optimal tightness may have been too tight. As such, the controller 102 can be configured to update the algorithm for calculating optimal tightness over time based on patient experience data. In another example, if a hematoma occurred during the procedure, the calculated optimal pressure decay curve may have been too high for too long, and the controller 102 can be configured to update the algorithm for calculating optimal pressures accordingly. In yet another example, if re-bleeds occurred during a procedure, the calculated optimal pressure or pressure decay curve may have been too low, and the controller 102 can update the algorithm for calculating optimal pressures accordingly.

While the method 150 of FIG. 10 is described as a series of steps in a particular order, in alternative embodiments, one or more steps may be eliminated or carried out in a different order. For example, in one alternative embodiment, one or both of steps 154, 156 may be completed before step 152. In another alternative embodiment, step 152 may be eliminated entirely. In such embodiment, the controller 102 may instead use stored, general population data in order to calculate optimized balloon pressures and pressure decay. For example, such general population data may be based upon clinical research of subjects with various BMIs, MAPs, and ACTs.

In light of the above, in the present embodiment, the band monitoring system 40 can be used during a hemostatic procedure to monitor hemostasis band performance to optimize its use. In some embodiments, the band monitoring system 40 can further be used for training. Accordingly, in one embodiment, the controller 102 can control the application to provide a prompt to the user to select between monitoring and training. For example, during monitoring, session data can be downloaded post-procedure and feedback can be received to optimize algorithms for determining optimal tension and pressure. On the other hand, during training, session data can be downloaded after a training session, though the trainee may not be prompted for patient feedback.

By way of example, FIGS. 12A-12C illustrate graphical user interfaces 196,198,200 of an application on a remote device 110, in accordance with one embodiment. When the user opens the application on the remote device 110, the remote device 110 can search for a connection (e.g., wired or wireless) to the monitoring unit 48. FIG. 12A illustrates a graphical user interface 196 that shows this initial application startup. Once the remote device 110 detects the monitoring unit 48, the graphical user interface 198 can be displayed, as shown in FIG. 12B, notifying the user as such and providing a prompt for the user to continue. If the user selects to continue, the graphical user interface 200 can be displayed, as shown in FIG. 12C, which can prompt the user to select a monitoring session or a training session.

While embodiments of the disclosure are illustrated and described herein with respect to the prior art hemostasis band 10 of FIG. 1, it should be noted that the systems and methods discussed herein may be used with any prior art hemostasis band 10. Additionally, it should be understood that, while the concepts discussed in the present disclosure generally relate to hemostasis bands indicated for use around a patient's wrist 42, these concepts have applicability to other hemostatic devices that may be employed elsewhere on a patient's body, for example on any portion of any limb or the torso, neck, or head. As one non-limiting example, the concepts discussed herein may be applicable to a tibiopedal vascular closure band, as described in U.S. patent application Ser. No. 16/442,009, filed Jun. 14, 2019, the entire contents of which is incorporated herein by reference. Finally, it should be understood that any of the features disclosed herein could be combined, mutatis mutandis, in alternative embodiments according to the present disclosure.

Presently, hemostatic procedures are performed using hemostasis bands with few restrictions upon the applied band tightness or the applied balloon pressure. Clinicians are left to their own experiences and/or limited training to use the hemostasis band optimally (e.g., so that the patient does not experience a re-bleed, hematoma, or a long-term radial artery occlusion, or is uncomfortable due to band placement). In light of the above, the present invention overcomes these drawbacks by providing a band monitoring system that includes feedback to the clinician, for example, via the clinician's mobile phone, for optimal band tightness and applied balloon pressure specific to the patient. As a result, the band monitoring system can reduce hematomas, long-term radial artery occlusions, and re-bleeds, and lower treatment costs.

While the principles of the claimed invention have been described above in connection with specific embodiment(s), it is to be clearly understood that this description is made only by way of example and not as a limitation of the scope of the invention, as set forth in the appended claims.

The invention claimed is:

1. A hemostatic device comprising:
   a hemostasis band including
      a main body adapted to be wrapped and releasably secured around at least one portion of a body part of a patient, and
      a compression element adapted to apply a targeted pressure to at least one artery or vein located in the body part; and
   a hemostasis band monitoring system including a pressure monitoring component incorporating a first sensor, the first sensor being adapted to detect a first measurement indicative of the targeted pressure that is being applied to the at least one artery or vein,
      the hemostasis band monitoring system further including a tension monitoring component incorporating a second sensor, the tension monitoring component adapted to be placed at least partially interior to the main body, the second sensor being adapted to detect a second measurement indicative of a tightness of the main body when the main body is wrapped and releasably secured around the at least one portion of the body part, the hemostasis band monitoring system further comprises a controller in communication with the second sensor, the controller being configured to receive the second measurement from the second sensor, compare the second measurement to an optimal tightness of the main body, and provide feedback to a user regarding whether the comparison indicates that the second measurement is greater than the optimal tightness.

2. The hemostatic device of claim 1, wherein the controller is also in communication with the first sensor, the controller being configured to receive the first measurement from the first sensor, compare the first measurement to an optimal pressure, and provide feedback to the user regarding the comparison.

3. The hemostatic device of claim 2, wherein the hemostasis band monitoring system further comprises a monitoring unit that houses the first sensor, the second sensor, and the controller.

4. The hemostatic device of claim 3, wherein the monitoring unit further comprises a transmitter/receiver, wherein the controller is configured to communicate with a remote device via the transmitter/receiver to provide the feedback to the user.

5. The hemostatic device of claim 3, wherein the monitoring unit further comprises a communication interface configured to provide the feedback to the user.

6. The hemostatic device of claim 5, wherein the communication interface includes at least one of an LED, a sound device, a display, a graphical user interface, and a touch screen.

7. The hemostatic device of claim 2, wherein the controller is further configured to receive an input including at least one item of inputted patient data and determine the optimal pressure based at least in part on the at least one item of inputted patient data.

8. The hemostatic device of claim 7, wherein the at least one item of inputted patient data includes at least one of body mass index, activated clotting time, or mean arterial pressure.

9. The hemostatic device of claim 8, wherein a weighting factor is assigned to at least one of the at least one item of inputted patient data to help calculate the optimal pressure.

10. The hemostatic device of claim 2, further comprising a data storage unit in communication with the controller, the data storage unit capable of storing data received from the first sensor.

11. The hemostatic device of claim 2, further comprising a housing configured to enclose the first sensor, the second sensor, and the controller, and a covering wrapped around the housing.

12. The hemostatic device of claim 2, further comprising a data storage unit in communication with the controller, the data storage unit capable of storing data received from at least one of the first sensor and the second sensor.

13. The hemostatic device of claim 1, wherein the tension monitoring component includes a tension pad having an internal cavity and a connector configured to fluidly couple the internal cavity to the second sensor.

14. The hemostatic device of claim 13, wherein the tension pad is configured to be positioned along the main body at a location opposite the compression element when the main body is wrapped around and releasably secured to the at least one portion of the body part.

15. The hemostatic device of claim 1, wherein the tension monitoring component is one of a mechanical, electrical, electromechanical, volumetric, and pneumatic pressure sensing mechanism.

16. The hemostatic device of claim 1, wherein the pressure monitoring component includes a three-way connector configured to fluidly couple an internal cavity of the compression element to the first sensor.

17. The hemostatic device of claim 16, wherein the three-way connector includes a first port configured to be coupled to the internal cavity of the compression element, a second port configured to be coupled to an inflation device, and a third port configured to be coupled to the first sensor.

18. A hemostatic device comprising:
a hemostasis band including
a main body adapted to be wrapped and releasably secured around at least one portion of a body part of a patient, and
an inflatable balloon assembly adapted to apply targeted pressure to at least one artery or vein located in the at least one portion of the body part; and
a hemostasis band monitoring system including
a first sensor adapted to sense a first measurement indicative of a tightness of the main body when it is wrapped and releasably secured around the at least one portion of the body part,
a second sensor adapted to sense a second measurement indicative of an internal pressure that is present within the inflatable balloon assembly, and
a controller in communication with the first sensor and the second sensor to receive the first measurement and the second measurement, respectively, the controller being configured to analyze the first measurement and the second measurement and provide feedback to a user relating the first measurement to an optimal tightness for the main body and relating the second measurement to an optimal internal pressure for the inflatable balloon assembly, the feedback relating the first measurement to the optimal tightness being any of indicating that the first measurement is greater than optimal tightness.

19. The hemostatic device of claim 18, wherein the hemostasis band monitoring system further includes a housing configured to house the first sensor, the second sensor, and the controller.

20. The hemostatic device of claim 19, wherein the housing includes a communication interface configured to provide the feedback to a user.

21. The hemostatic device of claim 18, wherein the first sensor is in communication with a compressible tension pad configured to be positioned between the main body and the at least a portion of the body part of the patient when the main body is wrapped and releasably secured around the at least one portion of the body part, wherein the first sensor is adapted to detect changes in an internal volume of the compressible tension pad due to tightening of the main body around the at least one portion of the body part.

22. The hemostatic device of claim 18, wherein the second sensor is in fluid communication with the inflatable balloon assembly and is adapted to detect changes in an internal pressure of the inflatable balloon assembly.

23. The hemostatic device of claim 18, wherein the controller is configured to transmit the feedback to a remote device, wherein the feedback is displayed to the user through a graphical user interface located on the remote device.

24. The hemostatic device of claim 18, wherein the controller is further configured to analyze at least one of the first measurement or the second measurement, and provide an alert to the user in response to at least one of the first measurement or the second measurement.

25. The hemostatic device of claim 18, wherein the controller is further configured to receive an input from the user including at least one item of patient data and determine the optimal internal pressure based at least in part on the at least one item of patient data.

26. The hemostatic device of claim 25, wherein the at least one item of patient data includes at least one of body mass index, activated clotting time, or mean arterial pressure.

* * * * *